(12) United States Patent
Brucker et al.

(10) Patent No.: US 7,758,634 B2
(45) Date of Patent: Jul. 20, 2010

(54) BIFURCATED STENT AND DELIVERY SYSTEM

(75) Inventors: Gregory G. Brucker, Minneapolis, MN (US); Enrique Malaret, Plymouth, MN (US); Todd Hall, Goshen, KY (US); David Byrd, Louisville, KY (US); Gerald Hubbs, Louisville, KY (US); Gregory Furnish, Louisville, KY (US); Josh Barber, Louisville, KY (US); Indaka Gunasekara, Louisville, KY (US); Benjamin Morris, Louisville, KY (US); Valerie Futral, Louisville, KY (US); Sava A. Chernomordik, Louisville, KY (US); William C. Mers Kelly, Crestwood, KY (US); William A. Reuss, Louisville, KY (US); Simon Furnish, New York City, NY (US); Michael A. Wilson, LeGrage, KY (US); Hacene Bouadi, Palo Alto, CA (US); John C. Muskivitch, Cupertino, CA (US); Matthew L. Pease, Mountain View, CA (US); David A. Rahdert, San Francisco, CA (US); Travis Rowe, Freemont, CA (US); Gregory M. Ruhf, Cupertino, CA (US); Brandon G. Walsh, Livermore, CA (US); Thomas Banks, Santa Barbara, CA (US); Russ Redmond, Goleta, CA (US); Claude Vidal, Santa Barbara, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 445 days.

(21) Appl. No.: 11/726,144

(22) Filed: Mar. 21, 2007
(Under 37 CFR 1.47)

(65) Prior Publication Data
US 2007/0168020 A1 Jul. 19, 2007

Related U.S. Application Data

(63) Continuation of application No. 11/028,754, filed on Jan. 3, 2005, now abandoned, which is a continuation of application No. 10/083,711, filed on Feb. 26, 2002, now abandoned.

(60) Provisional application No. 60/271,506, filed on Feb. 26, 2001, provisional application No. 60/271,602, filed on Feb. 26, 2001, provisional application No. 60/271,595, filed on Feb. 26, 2001.

(51) Int. Cl.
*A61F 2/06* (2006.01)

(52) U.S. Cl. .................................................. 623/1.35

(58) Field of Classification Search ................ 623/1.35, 623/1.11–1.12; 604/533–536; 606/108, 606/192, 194
See application file for complete search history.

(56) References Cited

U.S. PATENT DOCUMENTS

| | | | |
|---|---|---|---|
| 4,309,994 A | 1/1982 | Grunwald | |
| 4,769,005 A | 9/1988 | Ginsburg et al. | |
| 4,774,949 A | 10/1988 | Fogarty | |
| 4,896,670 A | 1/1990 | Crittenden | |
| 4,905,667 A | 3/1990 | Foerster et al. | |
| 4,994,071 A | 2/1991 | MacGregor | |
| 5,342,387 A | * 8/1994 | Summers | 606/198 |
| 5,387,235 A | 2/1995 | Chuter | |
| 5,456,712 A | 10/1995 | Maginot | |
| 5,476,471 A | 12/1995 | Shifrin et al. | |
| 5,487,730 A | 1/1996 | Marcadis et al. | |
| 5,562,641 A | * 10/1996 | Flomenblit et al. | 604/531 |
| 5,591,228 A | 1/1997 | Edoga | |
| 5,607,444 A | 3/1997 | Lam | |
| 5,609,605 A | 3/1997 | Marshall et al. | |
| 5,609,627 A | * 3/1997 | Goicoechea et al. | 128/898 |
| 5,613,980 A | 3/1997 | Chauhan | |
| 5,617,878 A | 4/1997 | Taheri | |
| 5,632,762 A | 5/1997 | Myler | |
| 5,632,763 A | 5/1997 | Glastra | |
| 5,632,772 A | 5/1997 | Alcime et al. | |
| 5,636,641 A | 6/1997 | Fariabi | |

| | | | |
|---|---|---|---|
| 5,653,743 A * | 8/1997 | Martin .................. 623/1.35 |
| 5,669,924 A | 9/1997 | Shaknovich ............ 623/1.11 |
| 5,669,932 A | 9/1997 | Fischell et al. |
| 5,676,697 A | 10/1997 | McDonald |
| 5,683,450 A | 11/1997 | Goicoechea et al. |
| 5,697,971 A | 12/1997 | Fischell et al. |
| 5,707,348 A | 1/1998 | Krogh |
| 5,709,713 A | 1/1998 | Evans et al. |
| 5,720,735 A | 2/1998 | Dorros |
| 5,725,519 A * | 3/1998 | Penner et al. .............. 606/1 |
| 5,749,825 A | 5/1998 | Fischell et al. |
| 5,749,890 A | 5/1998 | Shaknovich |
| 5,755,734 A | 5/1998 | Richter et al. |
| 5,755,735 A | 5/1998 | Richter et al. ............. 606/194 |
| 5,755,771 A | 5/1998 | Penn et al. |
| 5,755,773 A | 5/1998 | Evans et al. |
| 5,755,778 A | 5/1998 | Kleshinski |
| 5,782,906 A | 7/1998 | Marshall et al. ............ 623/1.15 |
| 5,824,036 A | 10/1998 | Lauterjung |
| 5,824,040 A | 10/1998 | Cox et al. |
| 5,827,320 A | 10/1998 | Richter et al. |
| 5,851,464 A | 12/1998 | Davila et al. |
| 5,868,777 A | 2/1999 | Lam |
| 5,893,887 A | 4/1999 | Jayaraman |
| 5,961,548 A | 10/1999 | Shmulewitz |
| 5,972,017 A * | 10/1999 | Berg et al. .............. 606/198 |
| 6,013,054 A | 1/2000 | Jium Yan |
| 6,017,324 A | 1/2000 | Tu et al. |
| 6,017,363 A | 1/2000 | Hojeibane |
| 6,030,414 A | 2/2000 | Taheri |
| 6,033,434 A | 3/2000 | Borghi |
| 6,033,435 A | 3/2000 | Penn et al. |
| 6,056,775 A | 5/2000 | Borghi et al. |
| 6,059,824 A | 5/2000 | Taheri |
| 6,068,655 A | 5/2000 | Seguin et al. |
| 6,071,298 A | 6/2000 | Lashinski .............. 606/198 |
| 6,086,611 A | 7/2000 | Duffy et al. |
| 6,093,203 A | 7/2000 | Uflacker |
| 6,096,073 A | 8/2000 | Webster et al. |
| 6,099,497 A | 8/2000 | Adams et al. |
| 6,113,579 A | 9/2000 | Eidenschink et al. |
| 6,117,117 A | 9/2000 | Mauch |
| 6,117,156 A | 9/2000 | Richter et al. |
| 6,129,738 A | 10/2000 | Lashinski et al. |
| 6,129,756 A * | 10/2000 | Kugler et al. ............ 623/1.27 |
| 6,142,973 A | 11/2000 | Carleton et al. |
| 6,143,002 A | 11/2000 | Vietmeier |
| 6,159,238 A | 12/2000 | Killion et al. |
| 6,165,195 A | 12/2000 | Wilson et al. |
| 6,168,621 B1 | 1/2001 | Vrba |
| 6,183,509 B1 | 2/2001 | Dibie |
| 6,197,049 B1 * | 3/2001 | Shaolian et al. ............ 623/1.35 |
| 6,203,568 B1 | 3/2001 | Lombardi et al. |
| 6,210,380 B1 | 4/2001 | Mauch |
| 6,210,429 B1 | 4/2001 | Vardi et al. |
| 6,210,433 B1 | 4/2001 | Larre |
| 6,221,098 B1 * | 4/2001 | Wilson et al. ............ 623/1.11 |
| 6,254,593 B1 | 7/2001 | Wilson |
| 6,258,115 B1 | 7/2001 | Dubrul |
| 6,258,116 B1 | 7/2001 | Hojeibane |
| 6,261,305 B1 | 7/2001 | Marotta et al. |
| 6,261,316 B1 | 7/2001 | Shaolian et al. |
| 6,264,662 B1 | 7/2001 | Lauterjung |
| 6,264,686 B1 | 7/2001 | Rieu et al. |
| 6,287,335 B1 * | 9/2001 | Drasler et al. ............ 623/1.28 |
| 6,290,673 B1 | 9/2001 | Shanley |
| 6,293,967 B1 * | 9/2001 | Shanley ................. 623/1.15 |
| 6,293,968 B1 | 9/2001 | Taheri |
| 6,325,822 B1 | 12/2001 | Vardi et al. |
| 6,325,826 B1 * | 12/2001 | Vardi et al. ............ 623/1.35 |
| 6,334,864 B1 | 1/2002 | Amplatz et al. |
| 6,346,089 B1 | 2/2002 | Dibie |
| 6,355,060 B1 | 3/2002 | Lenker et al. |
| 6,361,544 B1 | 3/2002 | Wilson et al. |
| 6,361,555 B1 | 3/2002 | Wilson |
| 6,383,213 B2 | 5/2002 | Wilson et al. ............ 623/1.11 |
| 6,387,120 B2 * | 5/2002 | Wilson et al. ............ 623/1.11 |
| 6,395,018 B1 | 5/2002 | Castaneda |
| 6,432,130 B1 * | 8/2002 | Hanson ................. 623/1.11 |
| 6,436,104 B2 | 8/2002 | Hojeibane |
| 6,436,134 B2 | 8/2002 | Richter et al. |
| 6,468,301 B1 | 10/2002 | Amplatz et al. ............ 623/1.13 |
| 6,508,836 B2 | 1/2003 | Wilson et al. |
| 6,517,558 B2 | 2/2003 | Gittings et al. |
| 6,520,988 B1 | 2/2003 | Colombo et al. |
| 6,540,779 B2 | 4/2003 | Richter et al. |
| 6,579,309 B1 * | 6/2003 | Loos et al. ............ 623/1.16 |
| 6,579,312 B2 | 6/2003 | Wilson et al. |
| 6,582,394 B1 | 6/2003 | Reiss et al. |
| 6,596,020 B2 | 7/2003 | Vardi et al. |
| 6,599,319 B2 | 7/2003 | Vardi et al. |
| 6,623,450 B1 * | 9/2003 | Dutta ................. 604/96.01 |
| 6,645,242 B1 | 11/2003 | Quinn |
| 6,673,107 B1 * | 1/2004 | Brandt et al. ............ 623/1.35 |
| 6,689,156 B1 | 2/2004 | Davidson et al. |
| 6,692,483 B2 | 2/2004 | Vardi et al. |
| 6,695,877 B2 * | 2/2004 | Brucker et al. ............ 623/1.16 |
| 6,706,062 B2 * | 3/2004 | Vardi et al. ............ 623/1.15 |
| 6,749,628 B1 | 6/2004 | Callol et al. |
| 6,761,734 B2 * | 7/2004 | Suhr ................. 623/1.35 |
| 6,776,793 B2 | 8/2004 | Brown et al. |
| 6,811,566 B1 | 11/2004 | Penn et al. |
| 6,835,203 B1 | 12/2004 | Vardi et al. |
| 6,858,038 B2 | 2/2005 | Heuser |
| 6,884,258 B2 | 4/2005 | Vardi et al. |
| 6,890,349 B2 * | 5/2005 | McGuckin et al. ............ 623/1.13 |
| 6,896,699 B2 | 5/2005 | Wilson et al. |
| 6,932,837 B2 | 8/2005 | Amplatz et al. |
| 6,945,995 B2 * | 9/2005 | Nicholas ................. 623/1.34 |
| 6,955,687 B2 | 10/2005 | Richter et al. |
| 6,955,688 B2 | 10/2005 | Wilson et al. |
| 6,962,602 B2 * | 11/2005 | Vardi et al. ............ 623/1.11 |
| 7,018,400 B2 | 3/2006 | Lashinski et al. |
| 7,056,323 B2 | 6/2006 | Mareiro et al. |
| 7,060,091 B2 | 6/2006 | Killion et al. |
| 7,220,275 B2 * | 5/2007 | Davidson et al. ............ 623/1.35 |
| 2001/0002443 A1 | 5/2001 | Parodi |
| 2001/0002927 A1 | 6/2001 | Detampel |
| 2001/0002943 A1 | 6/2001 | Nagayama et al. |
| 2001/0003161 A1 | 6/2001 | Vardi et al. |
| 2001/0004705 A1 | 6/2001 | Killion et al. |
| 2001/0004706 A1 | 6/2001 | Hojeibane |
| 2001/0004707 A1 | 6/2001 | Dereume et al. |
| 2001/0004823 A1 | 6/2001 | Cronin et al. |
| 2001/0007954 A1 | 7/2001 | Shaolian et al. |
| 2001/0012927 A1 | 8/2001 | Mauch |
| 2001/0016766 A1 | 8/2001 | Vardi et al. |
| 2001/0016767 A1 | 8/2001 | Wilson et al. |
| 2001/0016768 A1 | 8/2001 | Wilson et al. |
| 2001/0020173 A1 | 9/2001 | Klumb et al. |
| 2001/0020184 A1 | 9/2001 | Dehdashtian et al. |
| 2001/0025195 A1 | 9/2001 | Shaolian et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0039448 A1 | 11/2001 | Dibie |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0035392 A1 | 3/2002 | Wilson |
| 2002/0042650 A1 | 4/2002 | Vardi et al. |

| Publication No. | Date | Inventor |
|---|---|---|
| 2002/0052648 A1* | 5/2002 | McGuckin et al. ......... 623/1.35 |
| 2002/0072790 A1 | 6/2002 | McGuckin, Jr. et al. |
| 2002/0111675 A1 | 8/2002 | Wilson |
| 2002/0156516 A1 | 10/2002 | Vardi et al. |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1* | 11/2002 | Brucker et al. ............. 623/1.16 |
| 2002/0183763 A1 | 12/2002 | Callol et al. |
| 2002/0193872 A1 | 12/2002 | Trout, III et al. |
| 2002/0193873 A1* | 12/2002 | Brucker et al. ............. 623/1.35 |
| 2003/0009209 A1 | 1/2003 | Hojeibane |
| 2003/0028233 A1 | 2/2003 | Vardi et al. |
| 2003/0050688 A1 | 3/2003 | Fischell et al. |
| 2003/0055378 A1 | 3/2003 | Wang et al. |
| 2003/0055483 A1 | 3/2003 | Gumm |
| 2003/0074047 A1 | 4/2003 | Richter |
| 2003/0093109 A1 | 5/2003 | Mauch |
| 2003/0097169 A1 | 5/2003 | Brucker |
| 2003/0114912 A1 | 6/2003 | Sequin et al. |
| 2003/0125791 A1 | 7/2003 | Sequin et al. |
| 2003/0125802 A1 | 7/2003 | Callol et al. |
| 2003/0135259 A1 | 7/2003 | Simso |
| 2003/0181923 A1 | 9/2003 | Vardi |
| 2003/0191516 A1* | 10/2003 | Weldon et al. ............. 623/1.12 |
| 2003/0195606 A1 | 10/2003 | Davidson et al. |
| 2004/0006381 A1 | 1/2004 | Sequin et al. |
| 2004/0015227 A1 | 1/2004 | Vardi et al. |
| 2004/0044396 A1 | 3/2004 | Clerc et al. |
| 2004/0044398 A1* | 3/2004 | Nicholas ................... 623/1.16 |
| 2004/0059406 A1 | 3/2004 | Cully et al. |
| 2004/0088007 A1 | 5/2004 | Eidenschink |
| 2004/0098081 A1* | 5/2004 | Landreville et al. ........ 623/1.11 |
| 2004/0117003 A1 | 6/2004 | Ouriel et al. |
| 2004/0133268 A1 | 7/2004 | Davidson et al. |
| 2004/0138732 A1 | 7/2004 | Suhr et al. |
| 2004/0138737 A1* | 7/2004 | Davidson et al. .......... 623/1.35 |
| 2004/0148006 A1 | 7/2004 | Davidson et al. |
| 2004/0172121 A1 | 9/2004 | Eidenschink et al. |
| 2004/0186560 A1 | 9/2004 | Alt |
| 2004/0225345 A1 | 11/2004 | Fischell et al. |
| 2004/0267352 A1 | 12/2004 | Davidson et al. |
| 2005/0004656 A1 | 1/2005 | Das |
| 2005/0010276 A1* | 1/2005 | Acosta et al. ............. 623/1.11 |
| 2005/0010278 A1 | 1/2005 | Vardi et al. |
| 2005/0015108 A1 | 1/2005 | Williams et al. |
| 2005/0015135 A1 | 1/2005 | Shanley |
| 2005/0060027 A1 | 3/2005 | Khenansho et al. |
| 2005/0080474 A1* | 4/2005 | Andreas et al. ............ 623/1.11 |
| 2005/0096723 A1 | 5/2005 | Sequin et al. |
| 2005/0102021 A1 | 5/2005 | Osborne |
| 2005/0102023 A1 | 5/2005 | Yadin et al. |
| 2005/0119731 A1 | 6/2005 | Brucker et al. |
| 2005/0125076 A1 | 6/2005 | Ginn |
| 2005/0131526 A1 | 6/2005 | Wong |
| 2005/0149161 A1 | 7/2005 | Eidenschink et al. |
| 2005/0154442 A1 | 7/2005 | Eidenschink et al. |
| 2005/0154444 A1 | 7/2005 | Quadri |
| 2005/0183259 A1 | 8/2005 | Eidenschink et al. |
| 2005/0209673 A1 | 9/2005 | Shaked |
| 2005/0228483 A1 | 10/2005 | Kaplan et al. |
| 2006/0036315 A1 | 2/2006 | Yadin et al. |
| 2006/0041303 A1 | 2/2006 | Israel |
| 2006/0079956 A1 | 4/2006 | Eigler et al. |
| 2006/0173528 A1 | 8/2006 | Feld et al. |
| 2007/0073376 A1 | 3/2007 | Krolik et al. |
| 2007/0112418 A1* | 5/2007 | Eidenschink et al. ....... 623/1.35 |
| 2007/0112419 A1* | 5/2007 | Yadin ....................... 623/1.35 |
| 2007/0135904 A1* | 6/2007 | Eidenschink et al. ....... 623/1.35 |
| 2007/0168011 A1* | 7/2007 | LaDuca et al. ............. 623/1.11 |

FOREIGN PATENT DOCUMENTS

| | | |
|---|---|---|
| CA | 2220864 | 7/1999 |
| DE | 9014845 U1 | 2/1991 |
| DE | 2970883 | 3/1997 |
| DE | 29701758 | 5/1997 |
| EP | 0479730 | 10/1991 |
| EP | 0686379 | 12/1995 |
| EP | 0751752 | 1/1997 |
| EP | 0783873 | 7/1997 |
| EP | 0804907 | 11/1997 |
| EP | 0479557 | 7/1998 |
| EP | 0876805 B1 | 11/1998 |
| EP | 0647148 | 12/1998 |
| EP | 0880949 | 12/1998 |
| EP | 0891751 B1 | 1/1999 |
| EP | 0895759 A1 | 2/1999 |
| EP | 0897700 | 2/1999 |
| EP | 0904745 | 3/1999 |
| EP | 0937442 | 8/1999 |
| EP | 0347023 | 12/1999 |
| EP | 1031328 A1 | 8/2000 |
| EP | 1031329 | 8/2000 |
| EP | 1031330 | 8/2000 |
| EP | 0883384 | 12/2000 |
| EP | 0862392 | 8/2001 |
| EP | 0808140 | 12/2001 |
| EP | 0884028 B1 | 2/2002 |
| EP | 1190685 A2 | 3/2002 |
| EP | 0684022 B1 | 2/2004 |
| EP | 1157674 B1 | 7/2005 |
| EP | 1070513 B1 | 6/2006 |
| FR | 2678508 | 7/1991 |
| FR | 2740346 | 10/1995 |
| FR | 2756173 | 11/1996 |
| FR | 2760351 | 3/1997 |
| GB | 2337002 | 5/1998 |
| WO | 88/06026 | 8/1988 |
| WO | 9510442 | 4/1995 |
| WO | WO 95/14442 | 6/1995 |
| WO | 9521592 | 8/1995 |
| WO | 96/29955 | 10/1996 |
| WO | 9634580 | 11/1996 |
| WO | 9641592 | 12/1996 |
| WO | 9707752 | 3/1997 |
| WO | 9715346 | 5/1997 |
| WO | 9716217 | 5/1997 |
| WO | 97/26936 | 7/1997 |
| WO | 9741803 | 11/1997 |
| WO | 97/45073 | 12/1997 |
| WO | 9746174 | 12/1997 |
| WO | 9819628 | 5/1998 |
| WO | 9836709 | 8/1998 |
| WO | 9837833 | 9/1998 |
| WO | 9847446 | 10/1998 |
| WO | 9847447 | 10/1998 |
| WO | 9848879 | 11/1998 |
| WO | 9853759 | 12/1998 |
| WO | 9903426 | 1/1999 |
| WO | 9903462 | 1/1999 |
| WO | 9904726 | 2/1999 |
| WO | 9913808 | 3/1999 |
| WO | 99/15103 | 4/1999 |
| WO | 9915108 | 4/1999 |
| WO | 9915109 | 4/1999 |
| WO | 9924104 | 5/1999 |
| WO | 9934749 | 7/1999 |
| WO | 9936002 | 7/1999 |
| WO | 9936015 | 7/1999 |
| WO | 9944539 | 9/1999 |
| WO | 9956661 | 11/1999 |

| | | |
|---|---|---|
| WO | 9965419 | 12/1999 |
| WO | 0007523 | 2/2000 |
| WO | 0010485 | 3/2000 |
| WO | 0010489 | 3/2000 |
| WO | 0013613 | 3/2000 |
| WO | 0016719 | 3/2000 |
| WO | 0027307 | 5/2000 |
| WO | 0027463 | 5/2000 |
| WO | 0028922 | 5/2000 |
| WO | 0032266 | 6/2000 |
| WO | 0044307 | 8/2000 |
| WO | 0044309 | 8/2000 |
| WO | 0047134 | 8/2000 |
| WO | 0048531 | 8/2000 |
| WO | 0049951 | 8/2000 |
| WO | 0051523 | 9/2000 |
| WO | 0057813 | 10/2000 |
| WO | 00/71054 A1 | 11/2000 |
| WO | 0067673 | 11/2000 |
| WO | 0071055 | 11/2000 |
| WO | 0074595 | 12/2000 |
| WO | 0121095 | 3/2001 |
| WO | 0121109 | 3/2001 |
| WO | 0121244 | 5/2001 |
| WO | 0130433 | 5/2001 |
| WO | 0135715 | 5/2001 |
| WO | 0135863 | 5/2001 |
| WO | 0139697 | 6/2001 |
| WO | 0139699 | 6/2001 |
| WO | 0141677 | 6/2001 |
| WO | 0143665 | 6/2001 |
| WO | 0143809 | 6/2001 |
| WO | 0145594 | 6/2001 |
| WO | 0145785 | 6/2001 |
| WO | 0149342 | 7/2001 |
| WO | 0154621 | 8/2001 |
| WO | 0154622 | 8/2001 |
| WO | 0158385 | 8/2001 |
| WO | 0160284 | 8/2001 |
| WO | 0170294 | 9/2001 |
| WO | 0170299 | 9/2001 |
| WO | 0174273 | 10/2001 |
| WO | 0189409 | 11/2001 |
| WO | 02/00138 A2 | 1/2002 |
| WO | WO 02/39888 A2 | 5/2002 |
| WO | WO 02/39926 A2 | 5/2002 |
| WO | 02/053066 A1 | 7/2002 |
| WO | 02/068012 A2 | 9/2002 |
| WO | 03/007842 A2 | 1/2003 |
| WO | 03/055414 A1 | 7/2003 |
| WO | 03/063924 A1 | 8/2003 |
| WO | 2004/026174 A3 | 4/2004 |
| WO | 2004/026180 A2 | 4/2004 |
| WO | 2005/009295 A1 | 2/2005 |
| WO | 2005/014077 A2 | 2/2005 |
| WO | 2006/028925 A1 | 3/2006 |

OTHER PUBLICATIONS

U.S. Appl. No. 10/083,711, filed Feb. 26, 2002, Brucker et al.
U.S. Appl. No. 11/028,754, filed Jan. 3, 2005, Brucker et al.
Chevalier, M.D., Bernard, "Placement of Coronary Stents in Bifurcation Lesions by the "Culotte" Technique," the American Journal of Cardiology, vol. 82, pp. 943-949 (Oct. 15, 1998).
Nakamura M.D., Shigeru, "Techniques for Palmaz-Schatz Stent Deployment in Lesions with a Large Side Branch," Catheterization and Cardiovascular Diagnosis, vol. 34, pp. 353-361 (1995).
Caputo, Ronald P., "Stent Jail: A Minimum-Security Prison," The American Journal of Cardiology, vol. 77, pp. 1226-1230 (Jun. 1, 1996).
Colombo, M.D., Antonio, ""Kissing" Stent for Bifurcational Coronary Lesion," Catheterization and Cardiovascular Diagnosis, vol. 30, pp. 327-330 (Dec. 1993).
Carrie, M.D., Didier, ""T"-Shaped Stent Placement: A Technique for the Treatment of Dissected Bifurcation Lesions," Catheterization and Cardiovascular Diagnosis, vol. 37, pp. 311-313 (Mar. 1996).
Katoh, M.D., Osamu, "New Double Wire Technique to Stent Ostial Lesions," Catheterization and Cardiovascular Diagnosis, vol. 40, pp. 400-402 (Apr. 1997).
Lewis, M.D., Bruce E., "Acute procedural results in the treatment of 30 coronary artery bifurcation lesions with a double-wire atherectomy technique for side-branch protection," American Heart Journal, vol. 127:6, pp. 1600-1607 (Jun. 1994).
Yamashita, M.D.,PhD., Takehiro, "Bifurcation Lesions: Two Stents Versus One Stent—Immediate and Follow-up Results," Journal of the American College of Cardiology, vol. 35:5, pp. 1145-1151 (Apr. 2000).
Satler, M.D., Lowell F., "Bifurcation Disease: To Treat or Not to Treat," Catheterization and Cardiovascular Interventions, vol. 50, pp. 411-412 (2000).
U.S. Appl. No. 09/663,111, filed Sep. 15, 2000, Davidson et al.
U.S. Appl. No. 09/614,472, filed Jul. 11, 2000, Davidson et al.
U.S. Appl. No. 09/325,996, filed Jun. 4, 1999, Vardi et al.

\* cited by examiner

*Primary Examiner*—(Jackie) Tan-Uyen T Ho
*Assistant Examiner*—Son Dang
(74) *Attorney, Agent, or Firm*—Vidas, Arrett & Steinkraus P.A.

(57) ABSTRACT

A bifurcated stent includes a first stent section and a second stent section. The first stent section is balloon expandable, has an unexpanded configuration, an expanded configuration, and a tubular wall defining a secondary opening. The secondary stent section is self-expanding and an end of the secondary stent section is engaged to a portion of the tubular wall of the primary stent section defining the secondary opening. The secondary stent section has an unexpanded configuration with a first length and an expanded configuration with a second length where the first length is less than the second length. The secondary stent section is expanded to the expanded configuration after the primary stent section is expanded to the expanded configuration. The secondary stent section forms a portion of the tubular wall of the primary stent section in the unexpanded configuration.

8 Claims, 17 Drawing Sheets

BIFURCATED STENT AND DELIVERY SYSTEM

CROSS REFERENCE TO RELATED APPLICATIONS

This application is a continuation of Ser. No. 11/028,754, filed Jan. 3, 2005, which is a continuation of Ser. No. 10/083,711, filed Feb. 26, 2006, which claims priority from U.S. provisional applications 60/271,506 filed Feb. 26, 2001; U.S. provisional application 60/271,602 filed Feb. 26, 2001; and U.S. provisional application 60/271,595 filed Feb. 26, 2001; the entire content of each being incorporated herein by reference.

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding or expanded by an internal radial force, such as when mounted on a balloon.

Stents are generally tubular devices for insertion into body lumens. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Stents may be constructed from a variety of materials such as stainless steel, Elgiloy, nitinol, shape memory polymers, etc. Stents may also be formed in a variety of manners as well. For example a stent may be formed by etching or cutting the stent pattern from a tube or section of stent material; a sheet of stent material may be cut or etched according to a desired stent pattern whereupon the sheet may be rolled or otherwise formed into the desired tubular or bifurcated tubular shape of the stent; one or more wires or ribbons of stent material may be braided or otherwise formed into a desired shape and pattern.

A vessel having a stenosis may be viewed as an inwardly protruding arcuate addition of hardened material to a cylindrical vessel wall, where the stenosed region presents a somewhat rigid body attached along, and to, the elastic wall. The stenosis presents resistance to any expansion of the vessel in the region bridged by the stenosis. Stenoses vary in composition, for example, in the degree of calcification, and therefore vary in properties as well.

A stent may be used to provide a prosthetic intraluminal wall e.g. in the case of a stenosis to provide an unobstructed conduit for blood in the area of the stenosis. An endoluminal prosthesis comprises a stent which carries a prosthetic graft layer of fabric and is used e.g. to treat an aneurysm by removing the pressure on a weakened part of an artery so as to reduce the risk of embolism, or of the natural artery wall bursting. Typically, a stent or endoluminal prosthesis is implanted in a blood vessel at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to re-expand to a predetermined diameter in the vessel.

U.S. Pat. No. 4,886,062 discloses a vascular stent which comprises a length of sinuous or "zig-zag" wire formed into a helix; the helix defines a generally cylindrical wall which, in use, constitutes a prosthetic intraluminal wall. The sinuous configuration of the wire permits radial expansion and compression of the stent; U.S. Pat. No. 4,886,062 discloses that the stent can be delivered percutaneously and expanded in situ using a balloon catheter.

U.S. Pat. No. 4,733,665 discloses an expandable intraluminal graft which is constituted by a tubular member formed from a plurality of intersecting elongate members which permit radial expansion and compression of the stent.

EP-A-0556850 discloses an intraluminal stent which is constituted by a sinuous wire formed into a helix; juxtaposed apices of the wire are secured to one another so that each hoop of the helix is supported by its neighboring hoops to increase the overall strength of the stent and to minimize the risk of plaque herniation; in some embodiments the stent of EP-A-0556850 further comprises a tubular graft member to form an endoluminal prosthesis.

The devices cited above are generally satisfactory for the treatment of aneurysms, stenoses and other angeological diseases at sites in continuous unbifurcated portions of arteries or veins.

Within the vasculature however it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

In the case of an abdominal aortic aneurysm ("AAA") in the infrarenal portion of the aorta which extends into one of the common iliac arteries, the use of one of the prior art prosthesis referred to above across the bifurcation into the one iliac artery will result in obstruction of the proximal end of the other common iliac artery; by-pass surgery is therefore required to connect the one iliac artery in juxtaposition with the distal end of the prosthesis to the other blocked iliac artery. It will be appreciated by a person skilled in the art that it is desirable to avoid surgery wherever possible; the requirement for by-pass surgery associated with the use of the prior art prosthesis in juxtaposition with a bifurcation in an artery therefore constitutes a significant disadvantage.

Another example of a vessel bifurcation is the left and right common carotid arteries. These arteries are the principal arteries of the head and neck. Both of the common carotid arteries are quite similar and divide at a carotid bifurcation or bulb into an external carotid artery and an internal carotid artery. In the region of the carotid bulb and the ostium of the internal carotid artery, stenoses present a particular problem for carotid stenting due to the large tapering of the vessel interior from the common carotid artery (both the left and the right) to the internal carotid artery. The region of the carotid bifurcation or bulb happens to be where stenoses most often occur, particularly in the region of the ostium to the internal carotid artery in both of the carotid arteries.

Embodiments of the present invention relate to endoluminal prosthesis (stents) that may be utilized in the region of a bifurcation of vessels. The present invention also embraces stent connecting means for connecting a stent (e.g. a stent which forms part of an endoluminal prosthesis or bifurcated stent) to another stent or portion thereof. Some embodiments of the invention are directed to designs of bifurcated stents and their method of manufacture, as well as apparatuses and methods for introducing prostheses to the vasculature and methods of treating angeological diseases.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention includes many different embodiments. Various embodiments of the invention are directed to designs of bifurcated stents and/or the methods and apparatuses utilized to deliver a bifurcated stent to a bifurcation site.

In at least one embodiment, the invention is directed to a bifurcated stent delivery system that includes a unique catheter assembly having a primary and secondary guide wire wherein the secondary guide wire diverges away from the primary guide wire through a split in the catheter housing. The split allows the catheter to deliver a bifurcated stent center first.

The bifurcated stent is an embodiment of the invention that comprises a primary stent section and a secondary stent section. When used with the above catheter, the primary section is delivered center first through the split in the catheter housing. The secondary stent section is then delivered into a secondary vessel according to the predelivery placement of the secondary guide wire.

The bifurcated stent may be a one piece design where the primary and secondary sections are engaged to one another prior to delivery or it may be a two-piece design where the primary and secondary sections are separate and distinct stent bodies that may be optionally engaged to one another during delivery. The primary and secondary stent sections are preferably self-expandable but may be either self-expandable or balloon expandable independent of one another.

In another embodiment of the invention a self-expandable bifurcated stent may be delivered by a catheter having a retractable outer sheath or sleeve that retains the bifurcated stent in a collapsed state. When the sheath is retracted the primary stent section is exposed to self-expand. In at least one embodiment the secondary stent section remains in the collapsed state within the expanded primary stent section until a pusher mechanism is actuated to cause the secondary stent section to self-expand.

In at least one embodiment of the invention, a catheter system is employed wherein two guide wires and at least two balloons are employed to deliver a single piece bifurcated stent. In at least one embodiment, the balloons are substantially parallel to one another and the bifurcated stent is placed over both balloons with a single balloon extending into each section of the bifurcated stent. As a result, the stent branches may be independently guided and expanded. Where a portion of the stent is disposed about both balloons, in some embodiments the balloons may be linked together with a restrictive collar or band of material that will limit the expandability of the balloons to prevent the stent from being over expanded, however in other embodiments the collar may be omitted.

In some embodiments of the invention the catheter may also employ two angioplasty balloons that are initially advanced to the bifurcation site prior to stent delivery.

In at least one embodiment of the invention the bifurcated stent to be delivered is a one piece bifurcation stent comprising a primary stent section and a secondary stent section, the secondary stent section is linked to the primary stent section with one or more flexible linkage members. In at least one embodiment at least four linkage members connect the stent sections. Preferably, the flexible members are substantially S-shaped and/or are selectively annealed.

In at least one embodiment, the invention is directed to a single piece bifurcated stent wherein the primary stent section and the secondary stent section are engaged together by a linkage which allows the bifurcated stent to form distinct support structures on either side of the carina of a bifurcation. Preferably, the linkage comprises at least one strut or connecting member that is shared by both stent sections. In at least one embodiment the linkage is constructed from a selectively annealed metal or other material.

In the various embodiments of the invention portions of a given catheter and/or stent may include radiopaque materials to aid in visual inspection and/or placement of the devices such as during fluoroscopy.

Additional details and/or embodiments of the invention are discussed below.

BRIEF DESCRIPTION OF THE SEVERAL VIEWS OF THE DRAWINGS

A detailed description of the invention is hereafter described with specific reference being made to the drawings.

DETAILED DESCRIPTION OF THE INVENTION

As indicated above the present invention includes many different embodiments. In some embodiments the invention is directed to various designs of bifurcated stents, their delivery systems and methods of use.

Figure 1:
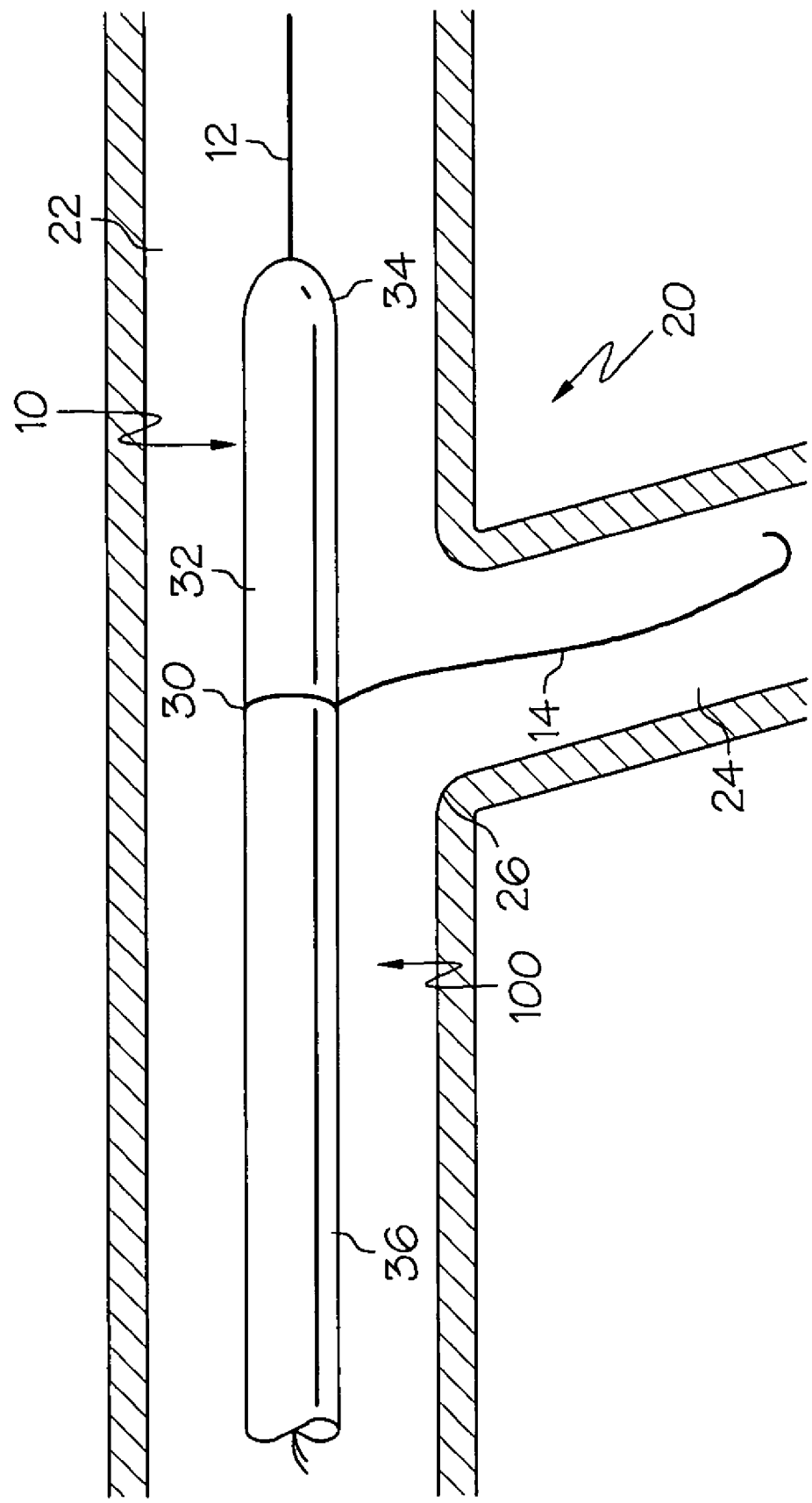
FIG. 1 is a side view of a distal portion of a stent delivery catheter positioned at a vessel bifurcation.

In FIG. 1 an embodiment of the invention is shown which comprises a bifurcated stent delivery system shown generally at 100. System 100 includes a catheter 10 that is advanced to a bifurcation site 20 along a primary guide wire 12 and a secondary guide wire 14. In use, the primary guide wire 12 and secondary guide wire 14 are advanced into a body lumen or vessel an advanced into the primary vessel 22. At the bifurcation site 20 the secondary guide wire 14 is directed into a secondary vessel 24 causing the guide wires 12 and 14 to diverge about the carina 26. Catheter 10 is advanced along the shared path of the guide wires 12 and 14 until it reaches the carina 26.

In order to accommodate the divergent path of the secondary guide wire 14, the catheter 10 includes a spilt area 30 where the secondary guide wire 14 exits the catheter 10. The spilt area 30 is a gap between two portions of the outer housing 32 of the catheter 10. The housing 32 may be characterized as a sheath, sleeve, sock or any other assembly suitable for retaining a stent in its collapsed state onto a stent receiving region of a catheter. Some examples of such stent retaining devices are described in U.S. Pat. No. 4,950,227 to Savin et al.; U.S. Pat. No. 5,403,341 to Solar; U.S. Pat. No. 5,108,416 to Ryan et al.; U.S. Pat. No. 5,968,069 to Dusbabek et al.; U.S. Pat. No. 6,068,634, to Cornelius et al.; U.S. Pat. Nos. 5,571,168; 5,733,267; 5,772,669; and 5,534,007 all of which are incorporated herein by reference in their entirety.

In the embodiment shown in FIG. 1, the housing 32 comprises a distal sleeve 34 and a proximal sleeve 36. As is more clearly shown in FIG. 2, sleeves 34 and 36 overlay a stent retaining region 38 of the catheter 10. Sleeves 34 and 36 may be self-retracting or include one or more pullback mechanisms (not-shown) such as are described in U.S. Pat. Nos. 5,571,135 and 5,445,646 both of which are incorporated herein by reference in their entirety.

Figure 2:
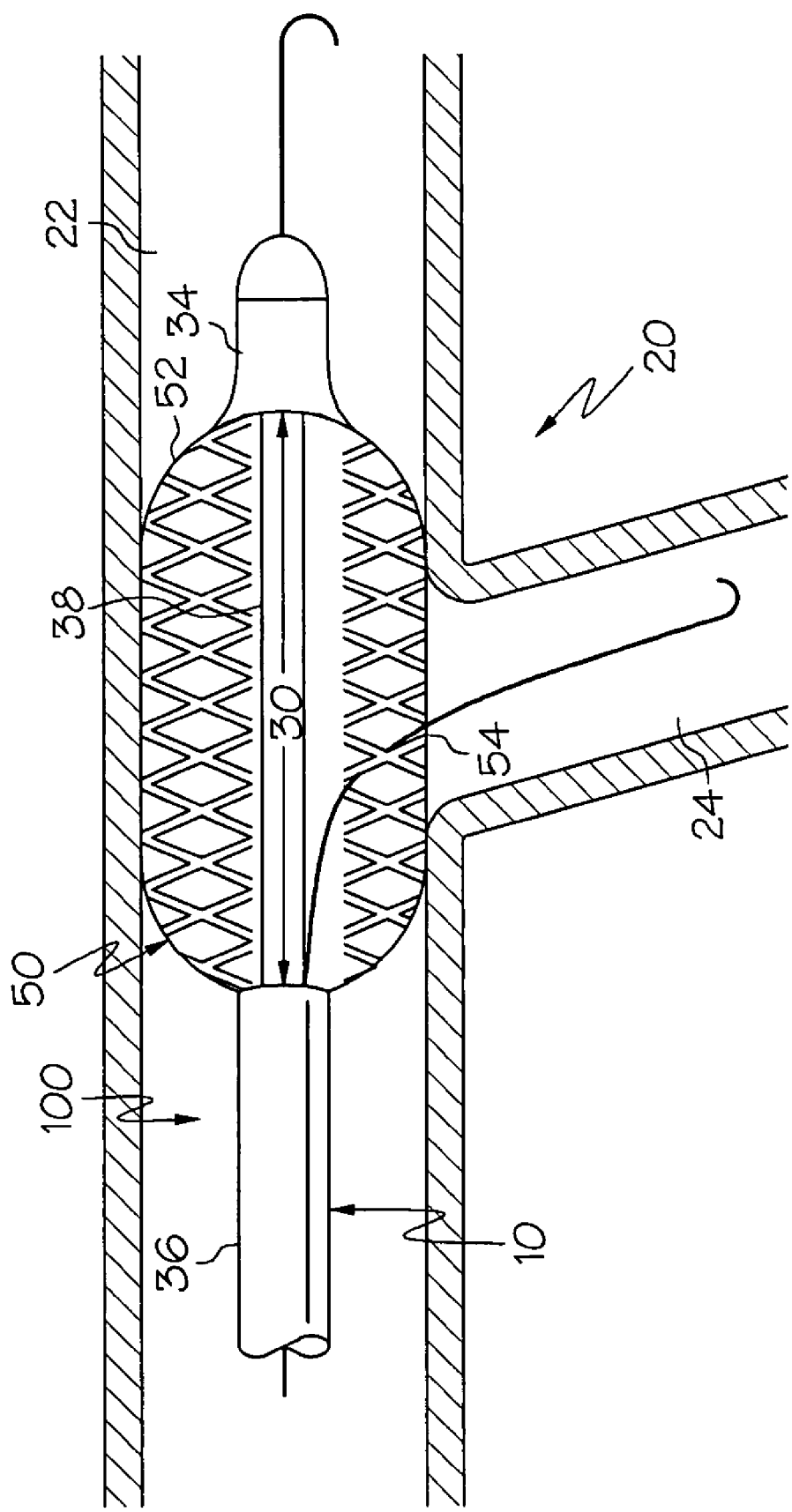
FIG. 2 is a side view of the catheter of FIG. 1 shown during initial delivery of a primary stent section of a bifurcated stent.

In FIG. 1, the sleeves 34 and 36 overlay the bifurcated stent 50, shown in FIG. 2, which is disposed about a stent retaining region 38. Stent retaining region 38 may include a balloon or other inflatable area for use in expanding and/or seating stent 50. Stent 50 may be balloon expandable, self-expanding or a hybrid type stent.

Figure 3:
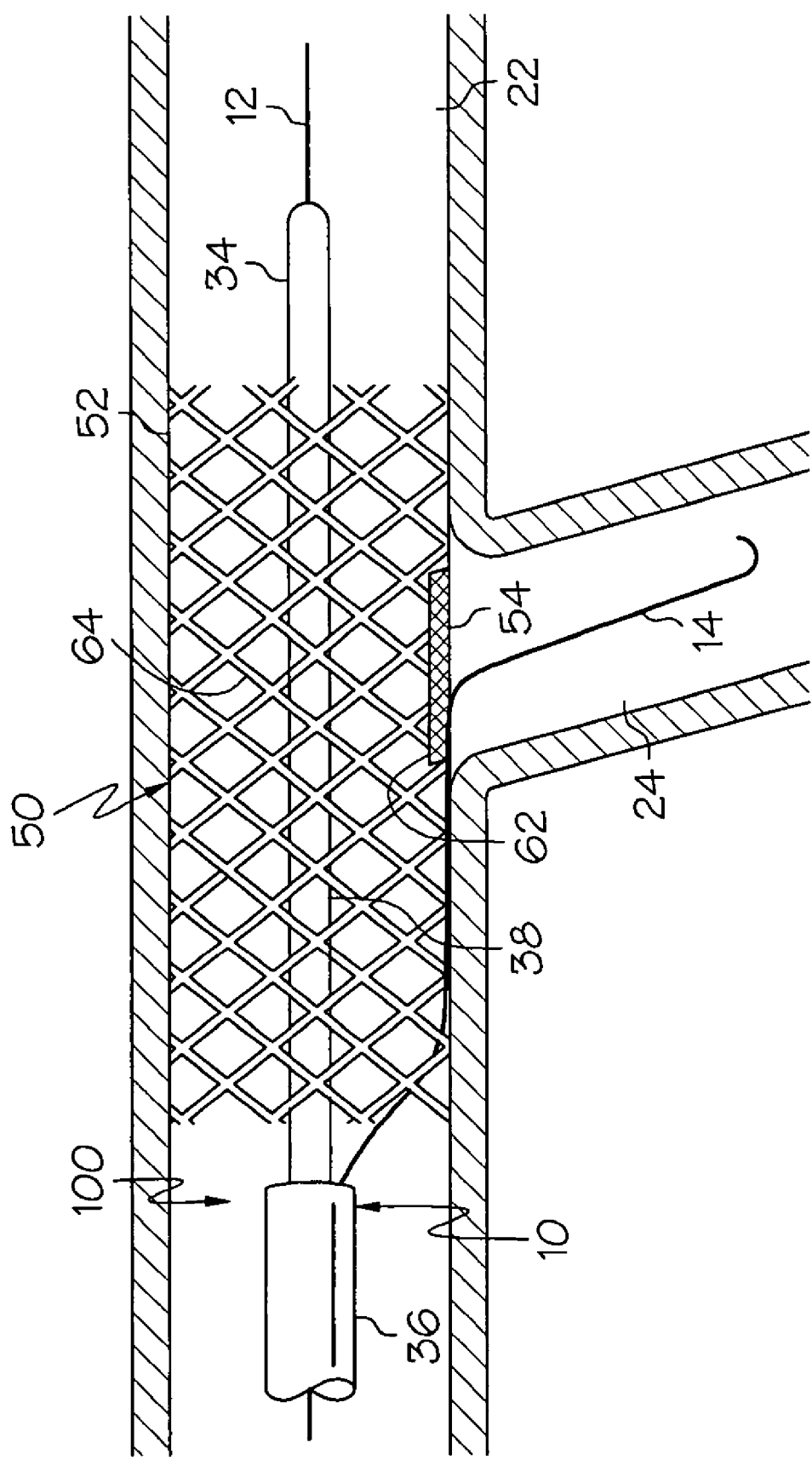
FIG. 3 is a side view of the catheter and bifurcated stent of FIG. 2 where the primary stent section is shown in the deployed state and a secondary stent section is shown in a predeployed state.
Figure 4:
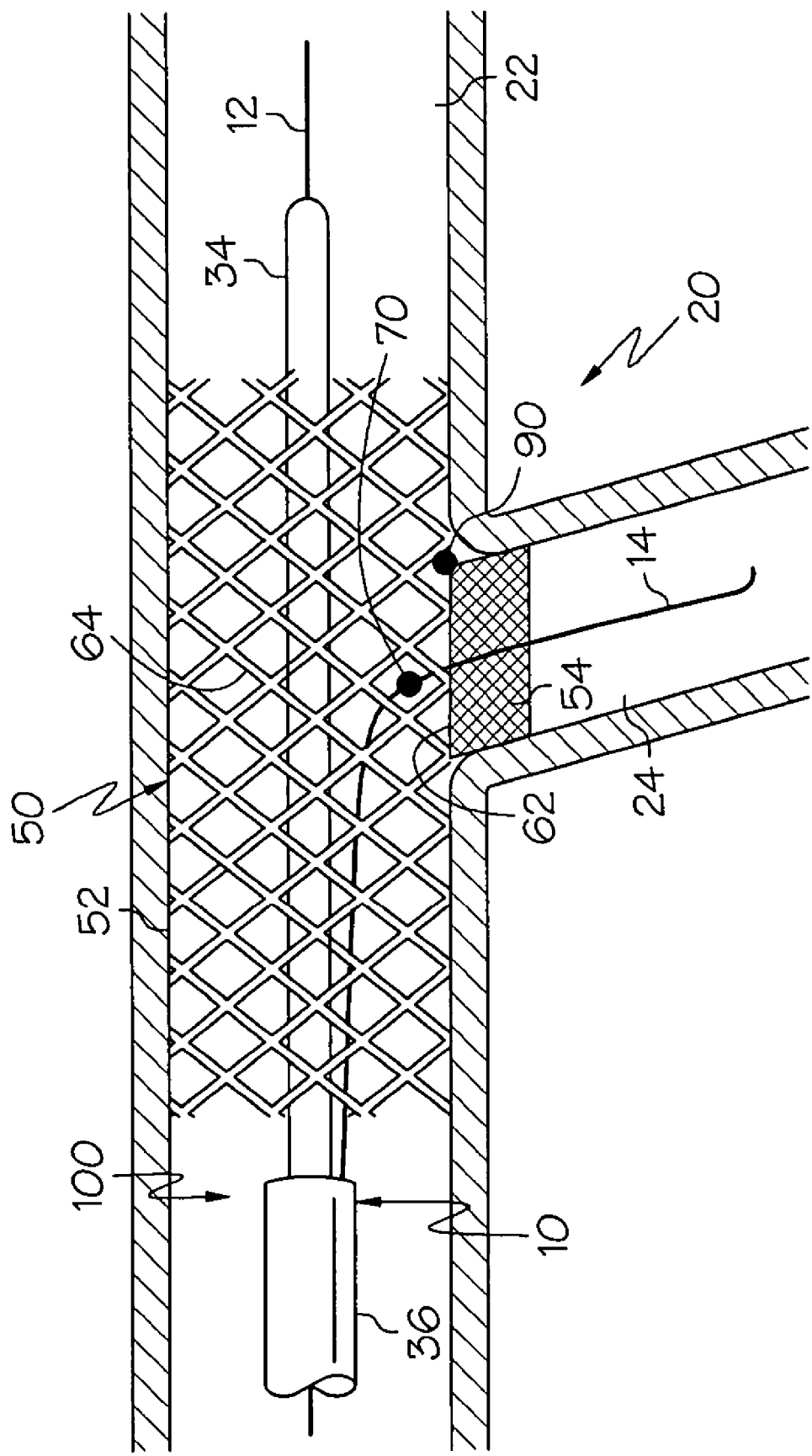
FIG. 4 is a side view of the catheter and bifurcated stent of FIG. 3 shown during initial delivery of the secondary stent section.

In the embodiments shown in FIGS. 2-4, the bifurcated stent 50 comprises a primary stent section 52 and a secondary stent section 54. Preferably, both sections 52 and 54 are self-expanding stent bodies though the individual stent sections may have different expansion characteristics as desired. In addition, the sections 52 and 54 of the bifurcated stent 50 may be individual stent bodies that are separately advanced and deployed forming stent 50 once they are fully deployed, or they may be integrally formed or otherwise connected prior to their deployment.

In the embodiment shown in FIG. 2, the housing portions or sleeves 34 and 36 have been withdrawn from about the bifurcated stent 50. As the sleeves 34 and 36 are withdrawn from the primary stent section 52 will begin to radially expand in a center first manner through the split area 30. When the sleeves 34 and 36 are fully withdrawn, such as is shown in FIG. 3 the primary stent section 52 is completely freed from the stent retaining region 38.

If the stent section 52 and 54 are not integral to each other or otherwise linked prior to delivery, upon expansion of the primary section 52 the secondary section may be advanced along the secondary guide wire 14 and advanced to an opening 62 in the wall 64 of the primary stent section 52. Opening 62 may be any diameter or shape but preferably is sized to accommodate the outer diameter of the secondary stent section 54 as well as the inner diameter of the secondary vessel 24.

Whether the secondary stent section 54 is engaged to the primary stent section 52 or separate therefrom prior to deployment, when the secondary stent section 54 is in position at opening 62 and the primary section 52 has been expanded, the secondary stent section 54 is then deployed into the secondary vessel 24, such as is shown in FIG. 4. The position of the stent 50 at the bifurcation site maybe visually established through the use of a radiopaque marker 90, discussed in greater detail below.

In at least one embodiment, where the secondary stent section 54 is at least partially constructed from a shape memory material, such as nitinol, the secondary stent section 54 will self expand according to a preprogrammed shape memory, such that the section both radially and longitudinally expands into the secondary vessel 24. In some embodiments, catheter 10 may include a pusher assembly 70 that is advanced along the secondary guide wire 14 to trigger expansion of the secondary stent section 54. Pusher assembly 70 may provide a stimulus which causes the section 54 to expand. Such a stimulus may be in the form of a simple mechanical engagement; delivery of an electrical current; or delivery of a predetermined temperature and/or a predetermined pH, such as by the release of a heated saline bolus. In some embodiments, a separate balloon catheter or other inflation device may be advanced along the secondary guide wire 14 to fully expand and/or seat the secondary stent section 54.

Figure 5:
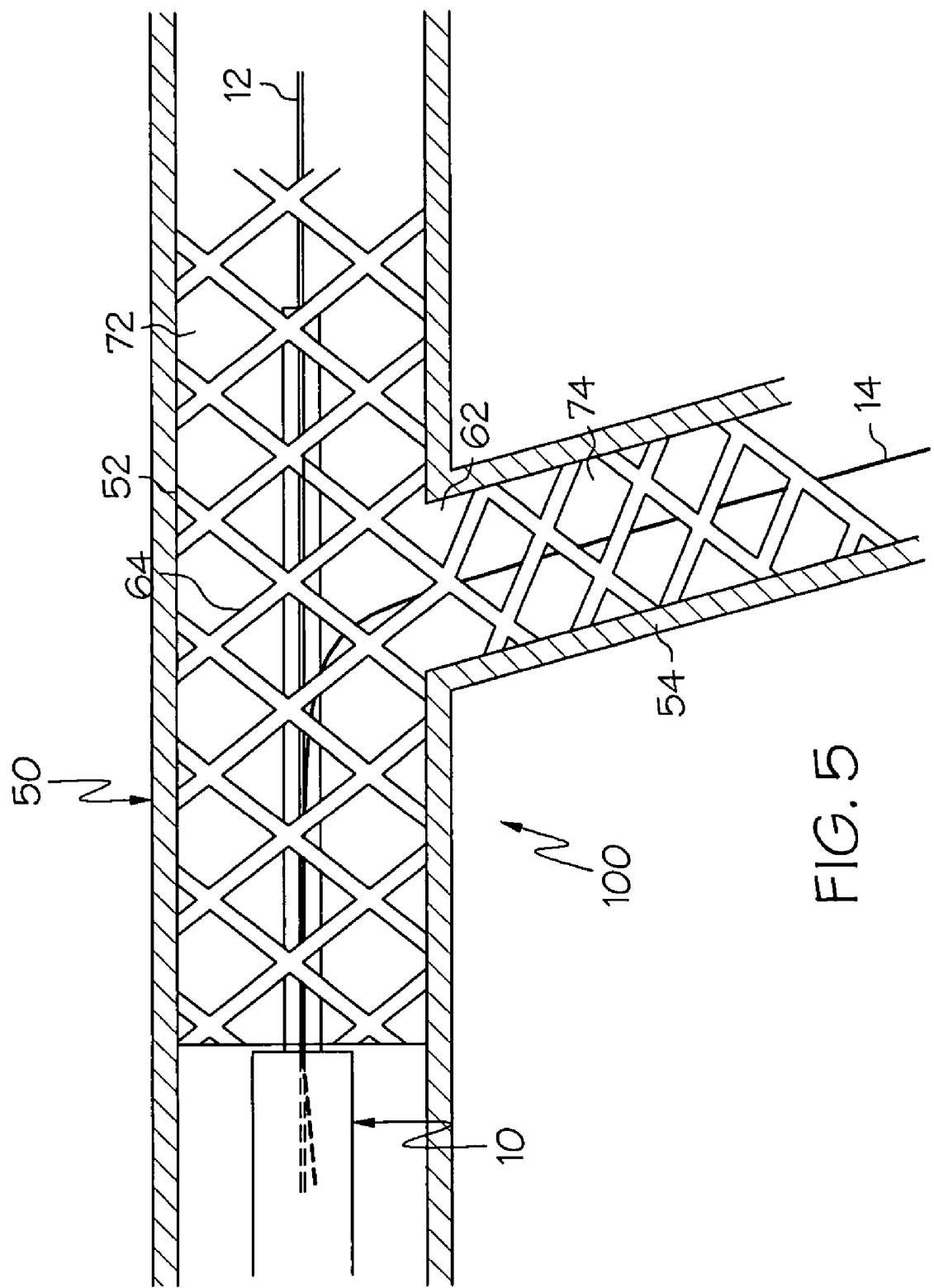
FIG. 5 is an enlarged side view of the catheter and stent shown in FIG. 4 wherein the primary and secondary stent sections are both shown in a deployed state.

When both stent sections 52 and 54 are fully deployed, such as is shown in FIG. 5, the proximal end of the secondary stent section 54 is preferably engaged to the wall 64 of the primary stent section 52. When fully deployed the primary stent section 52 defines a primary flow path 72 and the secondary stent section defines a secondary flow path 74 that is in fluid communication with the primary flow path via opening 62.

Figure 6:
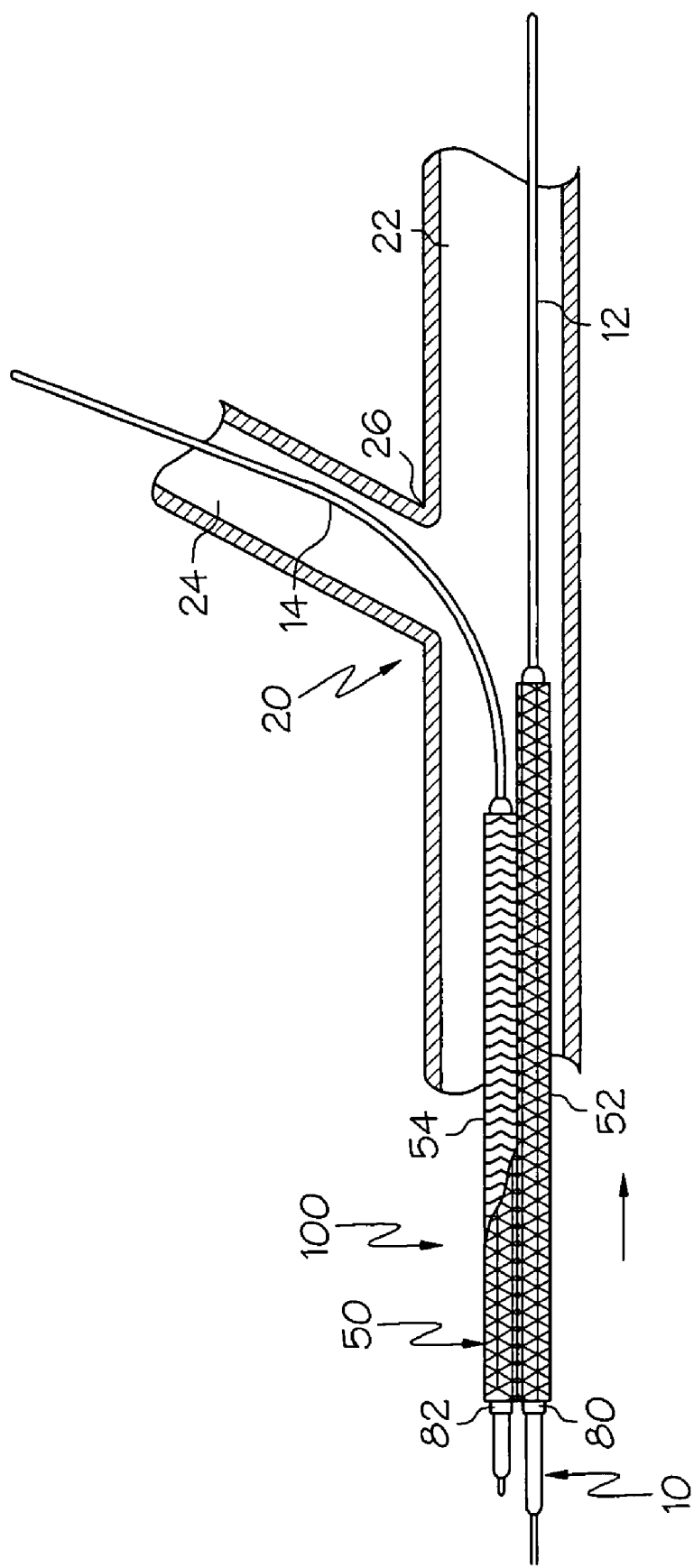
FIG. 6 is a side view of a bifurcated stent delivery system that includes two substantially parallel balloons and guide wires.

In an alternative embodiment of the invention, such as is shown in FIG. 6, system 100 may be provided with catheter 10 that is equipped with at least two balloons, a primary balloon 80 and a secondary balloon 82, which may be utilized for expansion and/or seating stent sections 52 and 54.

In the embodiment shown in FIG. 6, the bifurcated stent 50 may be constructed from stainless steel or other material that necessitates or would benefit from balloon expansion. As with previous embodiments, the catheter 10 includes a pair of guide wires 12 and 14 which are advanced to the bifurcation site 20 and which diverge at the carina 26 with the secondary guide wire 14 advancing into the secondary vessel 24.

Figure 9:
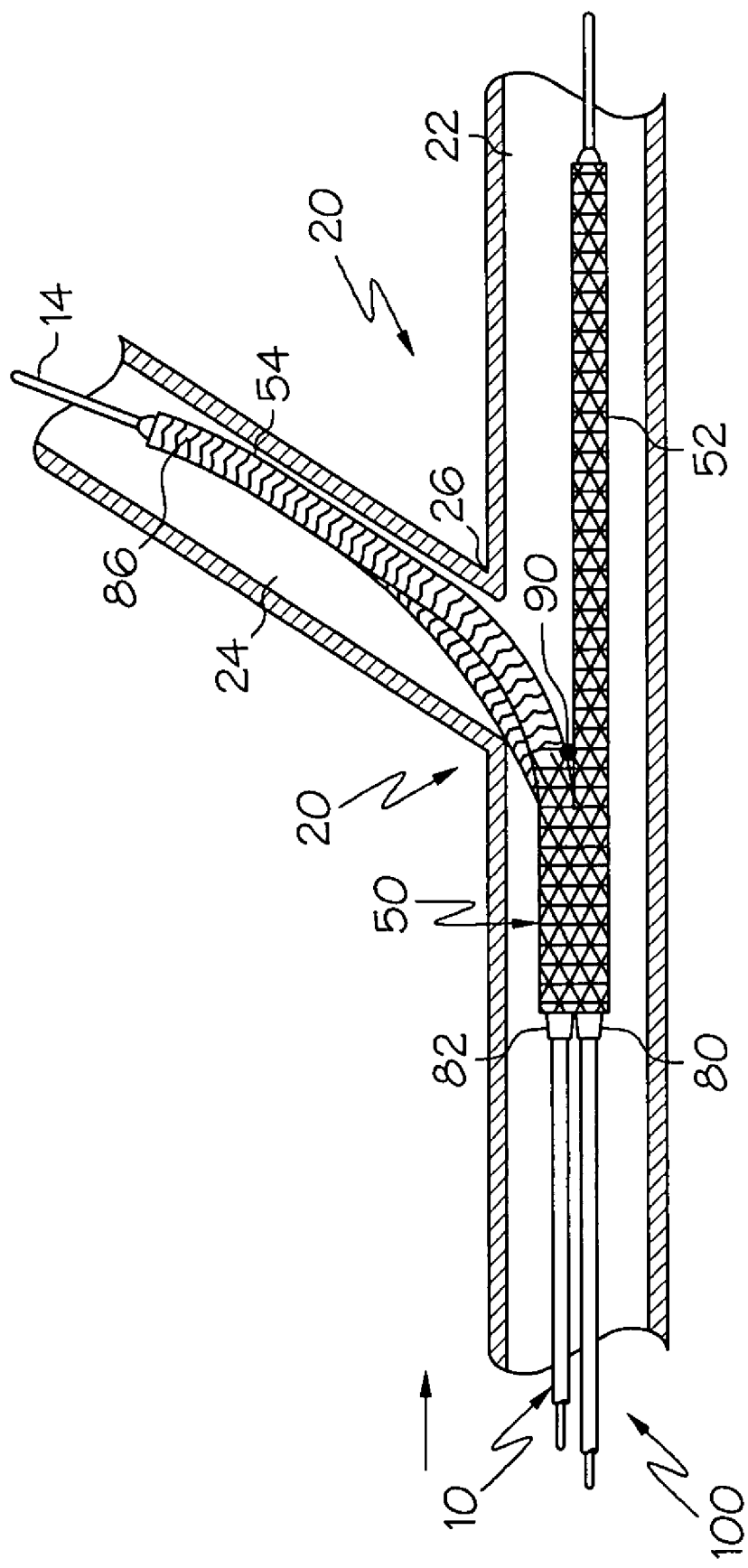
FIG. 9 is a side view of the system of FIG. 6 is shown being positioned at a bifurcation site prior to stent delivery.

In the embodiment shown in FIG. 6, during most of the advancement of the catheter 10 the balloons 80 and 82 are positioned together in the substantially parallel orientation shown. However, as the catheter 10 approaches the bifurcation site 20 the distal portion 86 of secondary balloon 82 and secondary stent section 54 are directed along the secondary guide wire 14 into the secondary vessel 24 as shown in FIG. 9.

In order to ensure that the bifurcated stent will provide adequate support to the vessels 22 and 24 of the bifurcation site, and particularly to the area of the carina 26, the catheter 10 may include a radiopaque marker 90. Marker 90 allows a practitioner to advance the catheter 10 to the bifurcation site 20 and visually determine through fluoroscopy or other means that the balloons 80 and 82 and stent sections 52 and 54 are properly positioned about the carina 26.

Marker 90 may be constructed from any radiopaque material and is preferably part of the bifurcated stent 50.

Figure 10:
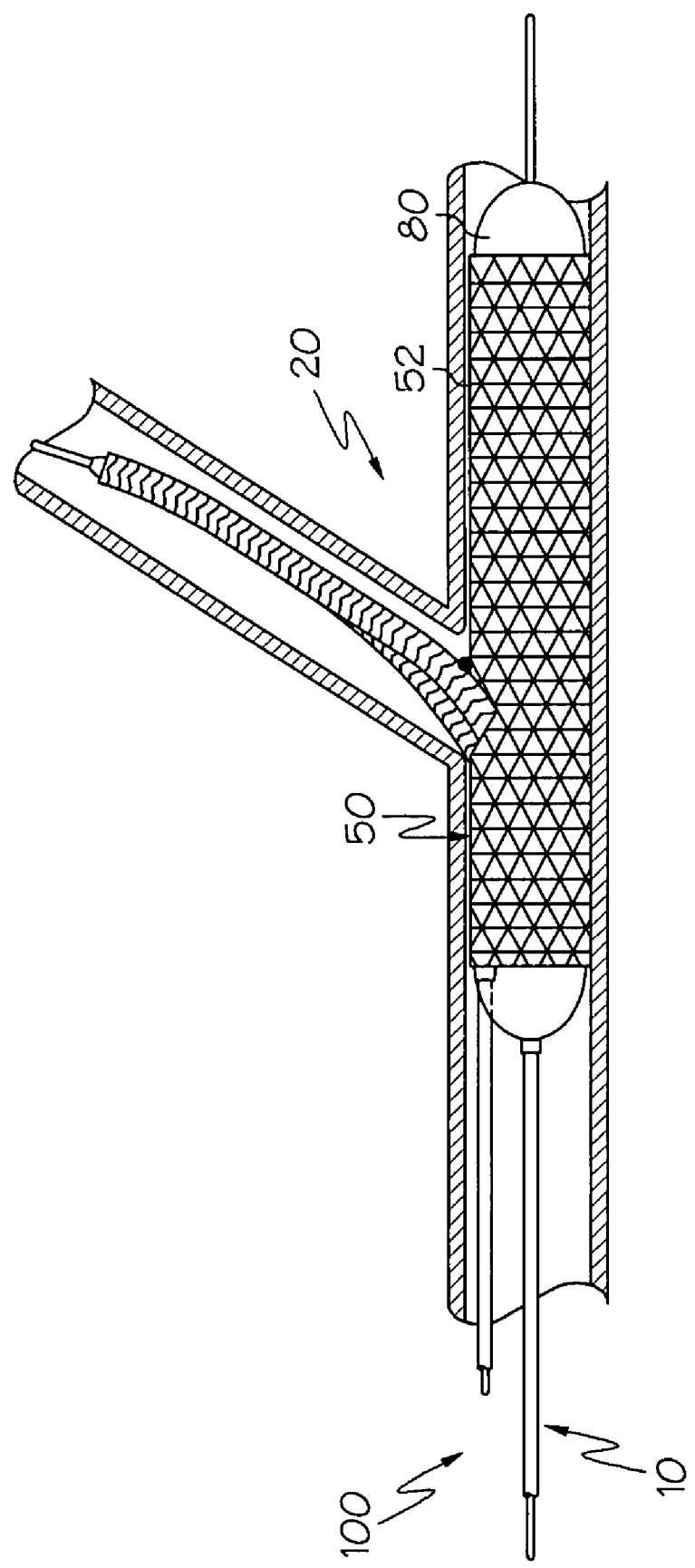
FIG. 10 is a side view of the system of claim 9 wherein a first balloon is shown inflated and a primary stent section is shown in an expanded state.
Figure 11:
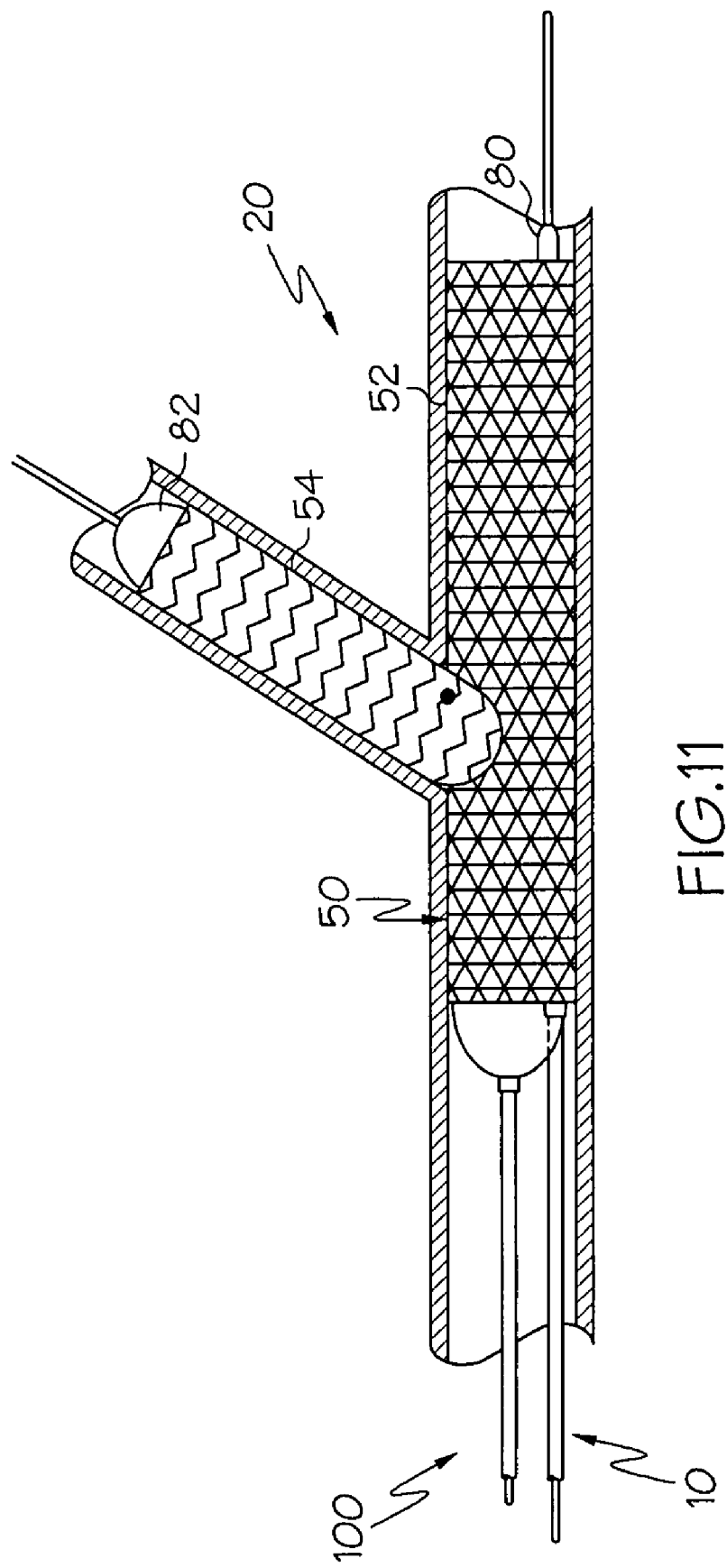
FIG. 11 is a side view of the system of claim 10 wherein a second balloon is shown inflated and a secondary stent section is shown in an expanded state.

Once it is determined that the stent 50 is in proper position at the bifurcation site 20, the primary balloon 80 is inflated to expand the primary stent section 52 as shown in FIG. 10. After the initial expansion of the primary stent section 52, the secondary balloon 82 is inflated to initially expand the secondary stent 54 shown in FIG. 11.

Figure 12:
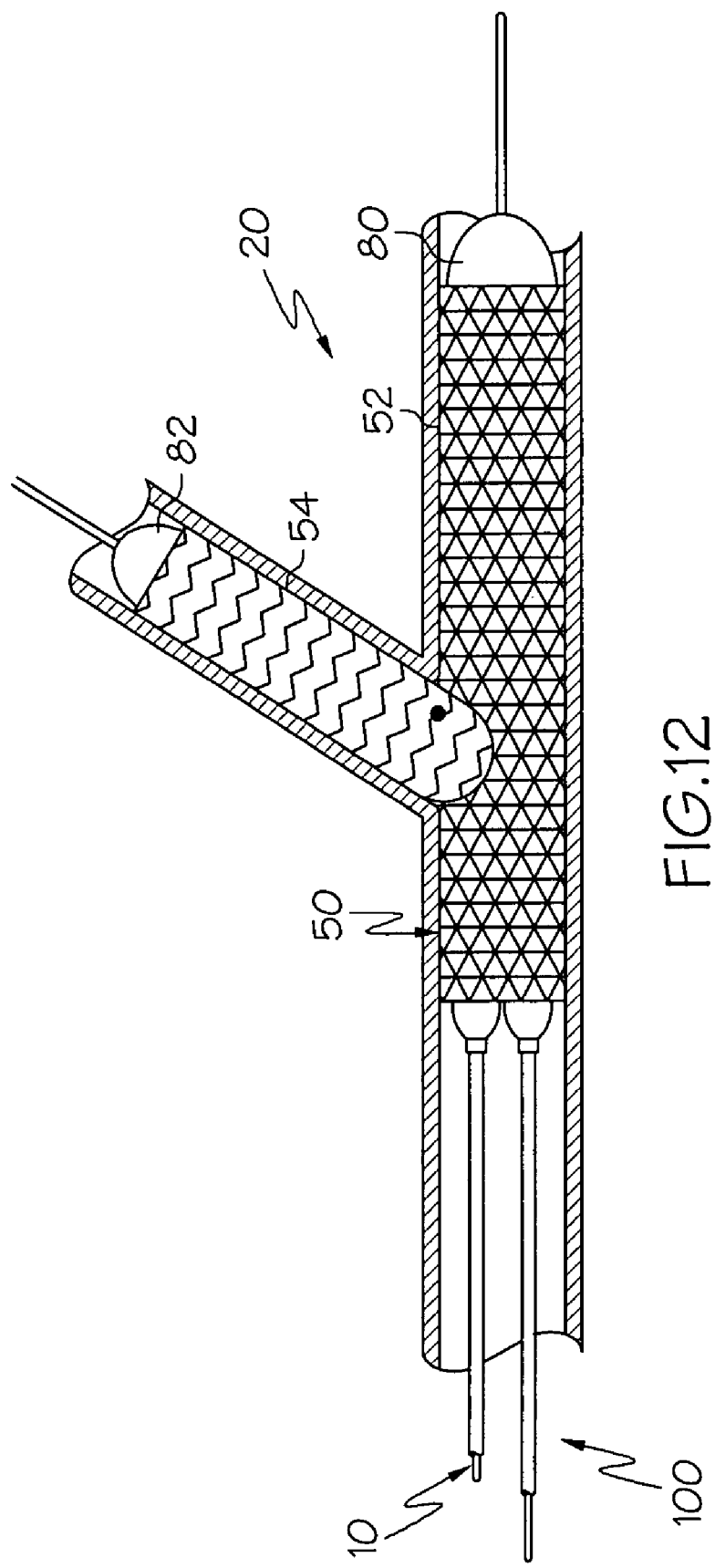
FIG. 12 is a side view of the system shown in FIG. 11 wherein both balloons are inflated.

In some embodiments it may be preferable to first deflate the primary balloon 80 before inflating the secondary balloon 82. In some embodiments where balloon 80 is deflated prior to inflation of balloon 82, balloon 80 may be subsequently inflated after inflation of balloon 82 to fully expand the stent and seat it in place within the bifurcation such as is shown in FIG. 12. Alternatively, balloons 80 and 82 may be inflated simultaneously.

Figure 13:
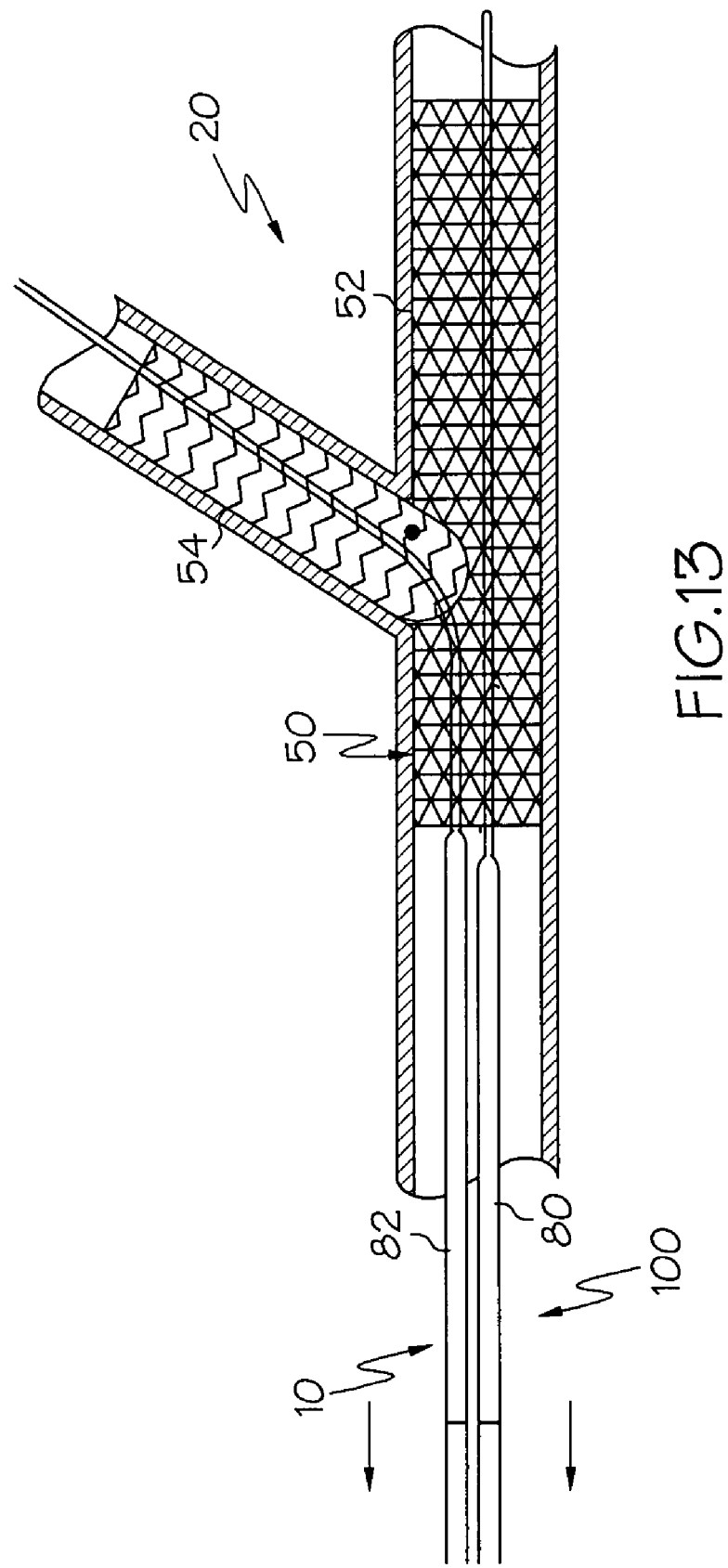
FIG. 13 is a side view of the system of claim 12 wherein the balloons are shown in an uninflated state prior to stent delivery and the sections of the bifurcated stent are shown in a deployed state.

Once both stent sections 52 and 54 are fully expanded, the balloons 80 and 82 are deflated and with drawn from the bifurcation site 20, such as is depicted in FIG. 13

Figure 7:
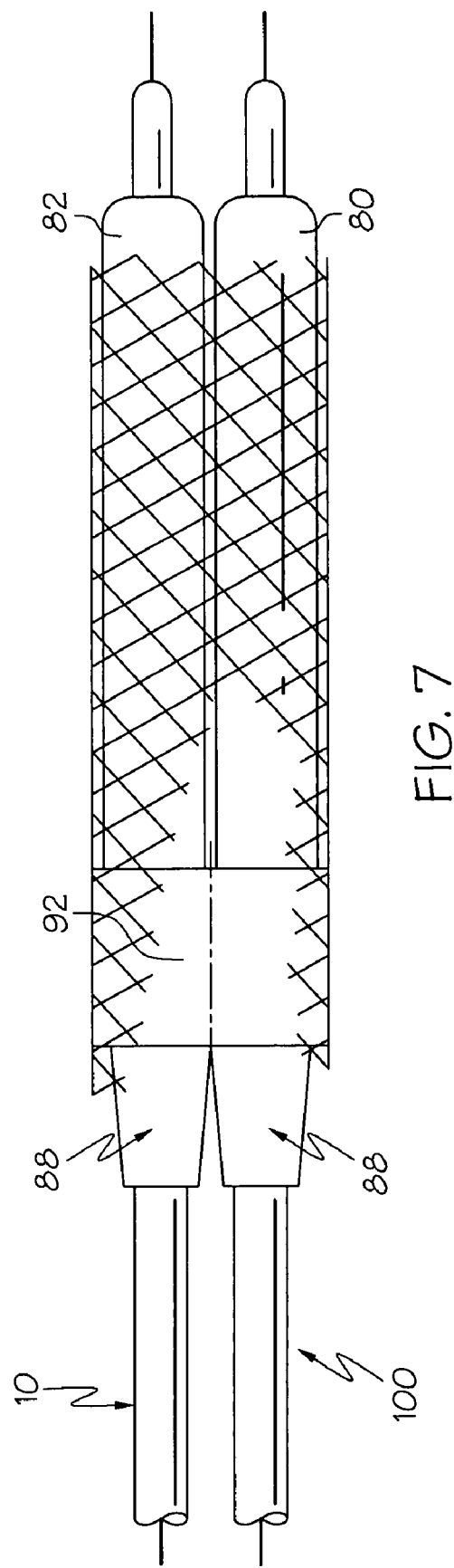
FIG. 7 is a side view of a bifurcated stent delivery system wherein the catheter includes a restrictive band where the stent is disposed about both balloons.

Because some bifurcated stents may be subject to distortion or damage when over expanded or subjected to high radially outward acting pressure, in some embodiments, such as shown in FIG. 7, the proximal portion 88 of balloons 80 and 82, where both balloons are contained within the primary stent section 52, the catheter 10 may employ a circumferential band 92 that will limit the expandability of the proximal portion 88 of balloons 80 and 82, thereby preventing over inflation and over expansion of the primary stent portion 54 when both balloons are inflated. Band 92 may be constructed from any minimally or non-expandable material such as polyethyleneterephthalate (PET) or stainless steel.

Figure 8:
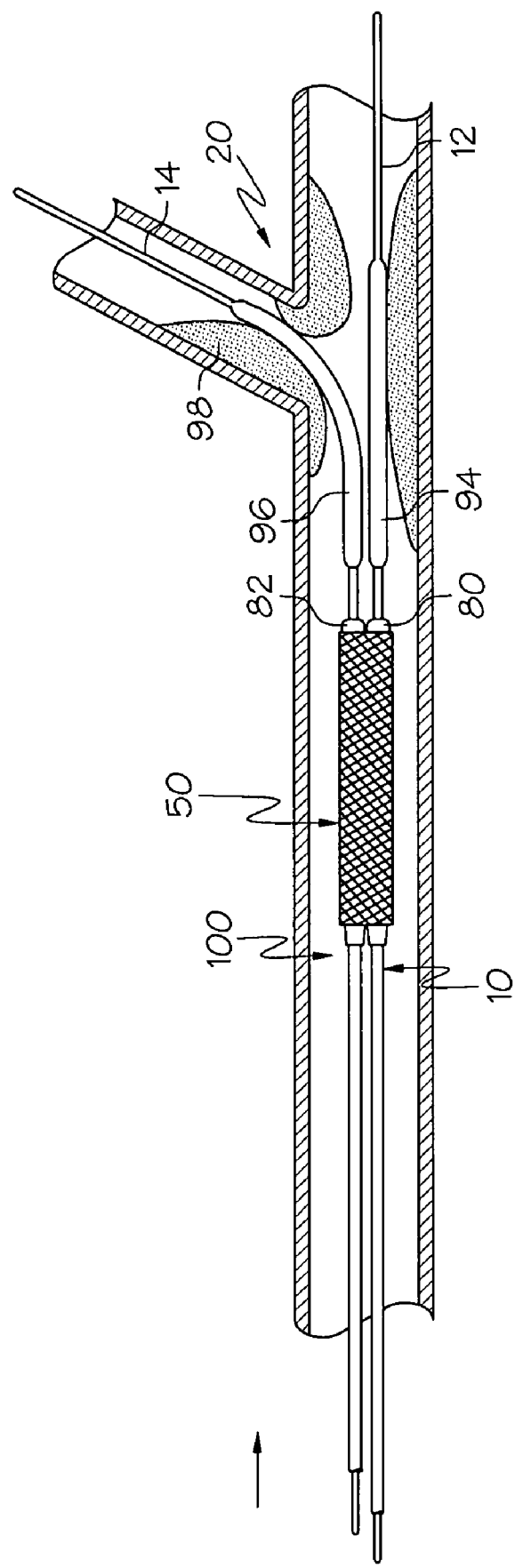
FIG. 8 is a side view of a stent delivery system wherein the system includes a pair of angioplasty balloons.

In some applications, it may be beneficial or necessary to conduct an angioplasty procedure prior to insertion of the bifurcated stent 50. As a result, in at least one embodiment of the invention, an example of which is shown in FIG. 8, the catheter 10 may be equipped with a primary angioplasty balloon 94 and a secondary angioplasty balloon 96. In practice balloons 94 and 96 may be initially advanced to the bifurcation site 20 along guide wires 12 and 14 respectively. Upon reaching the bifurcation site 20, the balloons 94 and 96 may be inflated to reduce any stenosis or blockage 98 that may be present. After the blockage 98 is reduced, the balloons 94 and 96 may be deflated and advanced along the guide wires 12 and 14 into the respective vessels 22 and 24 thereby allowing balloons 80 and 82 to be positioned at the bifurcation site 20 to delivery the bifurcated stent 50.

In the embodiments shown in FIGS. 6-13, the bifurcated stent 50 may be a single piece design, where sections 52 and 54 are engaged to one another prior to and after delivery; or the stent 50 may be a two-piece design where both sections 52 and 54 are independent stent bodies that are separate prior to delivery and which may continue to be separate or which may become engaged to one another during or after delivery.

Figure 14:
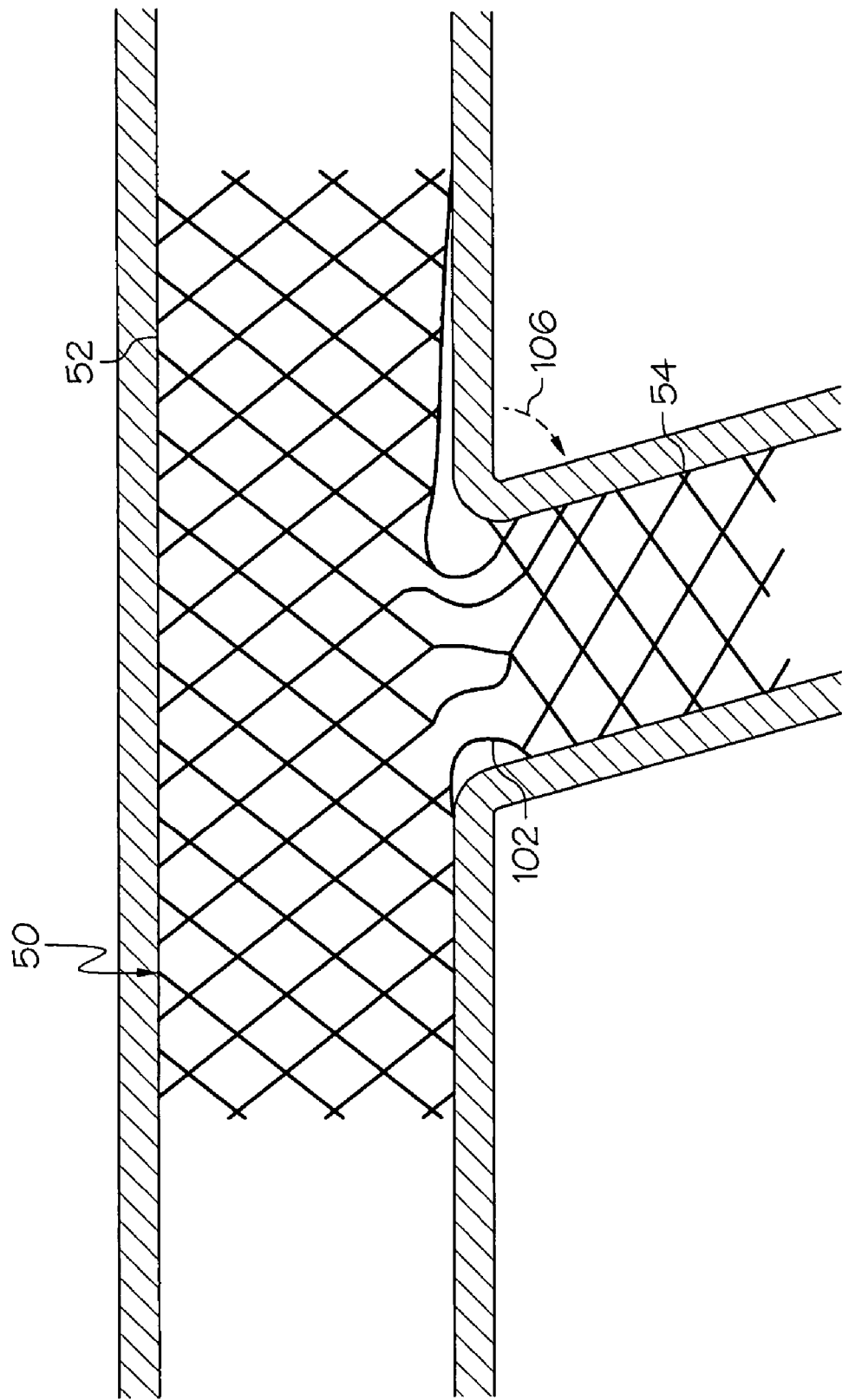
FIG. 14 is an enlarged side view of a bifurcated stent wherein the stent sections are connected by one or more linkage members.
Figure 15:
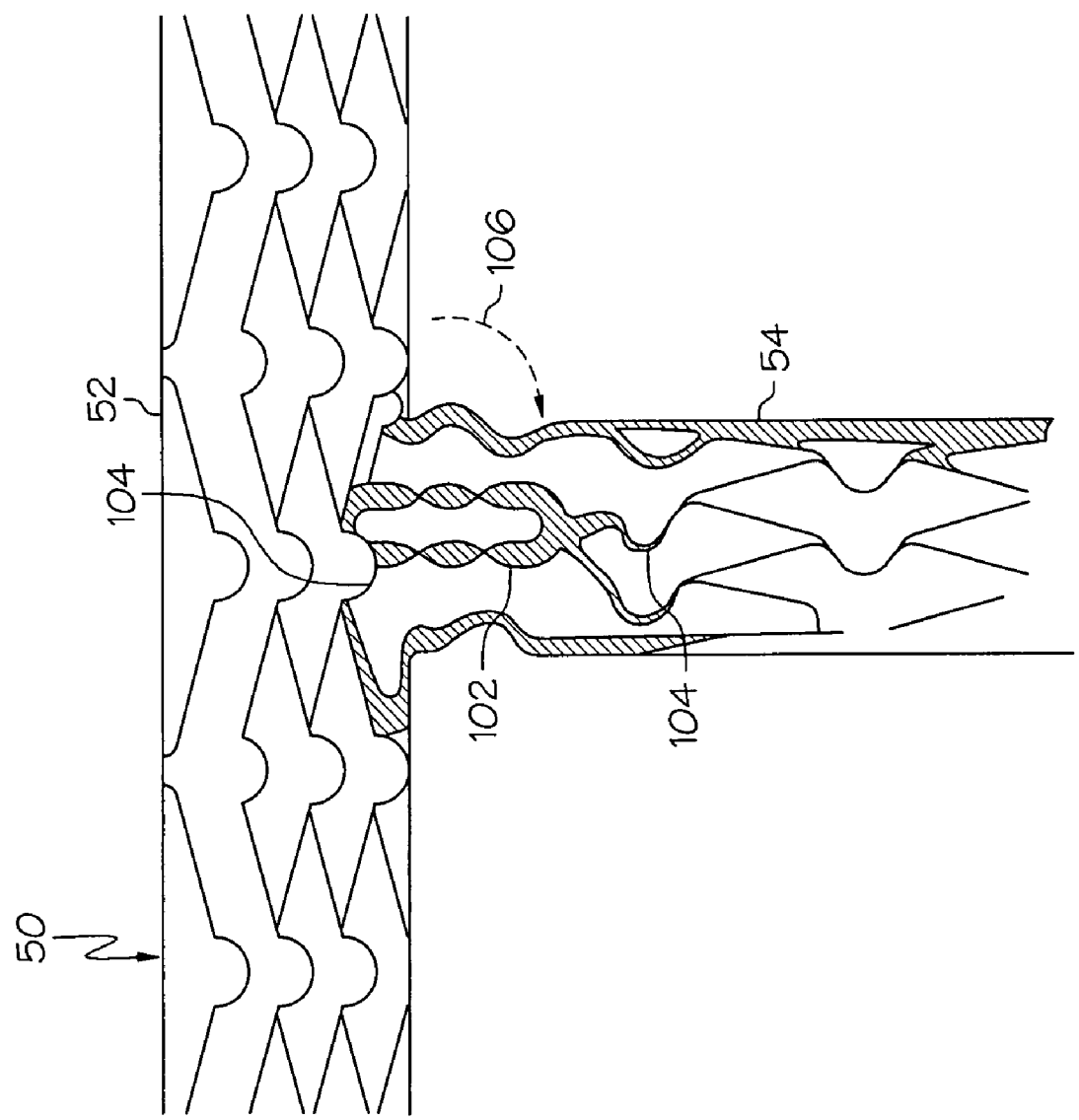
FIG. 15 is an enlarged side view of a bifurcated stent wherein the stent sections are connected by one or more linkage members.
Figure 16:
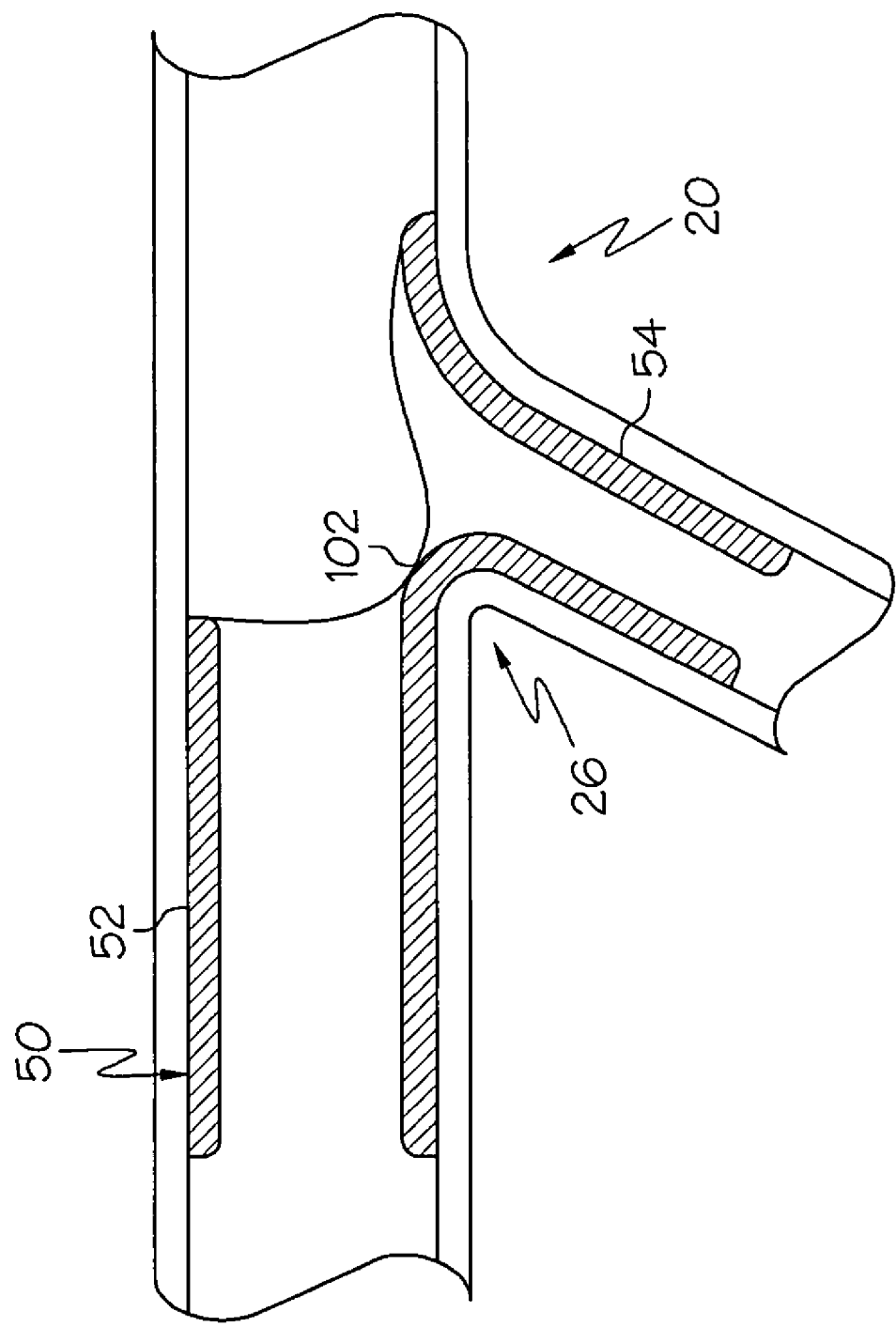
FIG. 16 is a side view of a bifurcated stent wherein the stent sections are connected by an actuated linkage assembly.

In embodiments where the stent 50 is a one-piece design, the stent sections may be engaged together by one or more linkage member 102 such as are shown in FIGS. 14-16. In FIGS. 14 and 15, the sections 52 and 54 are connected by at least 4 linkage members 102. In at least one embodiment, the sections 52 and 54 are connected by at least 8 linkage members 102. Linkage members 102 may be characterized as struts or connecting members 104 that are shared between sections 52 and 54. In a preferred embodiment, the members 102 are selectively annealed to provide the bifurcated stent 50 with improved flexibility between sections 52 and 54. By selectively annealing the members 102, the secondary stent section 52 may be articulated relative to the primary stent section 54 such that the bifurcated stent sections 52 and 54 may be provided with an angular relationship of about 90 degrees, indicated at reference numeral 106 in FIG. 15, or a more acute angle 108 shown in FIG. 14. By providing a bifurcated stent 50 that has sections 52 and 54 that may be oriented at a variety of angles, a single stent may be used to address a variety of different angular relationships between vessels of various bifurcation sites within a body. Preferably, the angular relationship between sections 52 and 54 defines an angle of about 10 degrees to about 120 degrees.

In at least one embodiment, the linkage members 102 are provided with a curvilinear or S-shaped configuration such as is best shown in FIG. 15. The S-shape of the linkage members aids in providing the bifurcated stent 50 with the ability to articulate about vessel junctions of various angles.

In at least one embodiment, shown in FIG. 16, the sections 52 and 54 of a bifurcated stent 50 are linked by a single linkage member 102. When inserted at a bifurcation site 20, the single linkage member is positioned at the carina 26 and acts as a hinge to allow the sections 52 and 54 to be disposed about the carina 26.

Figure 17:
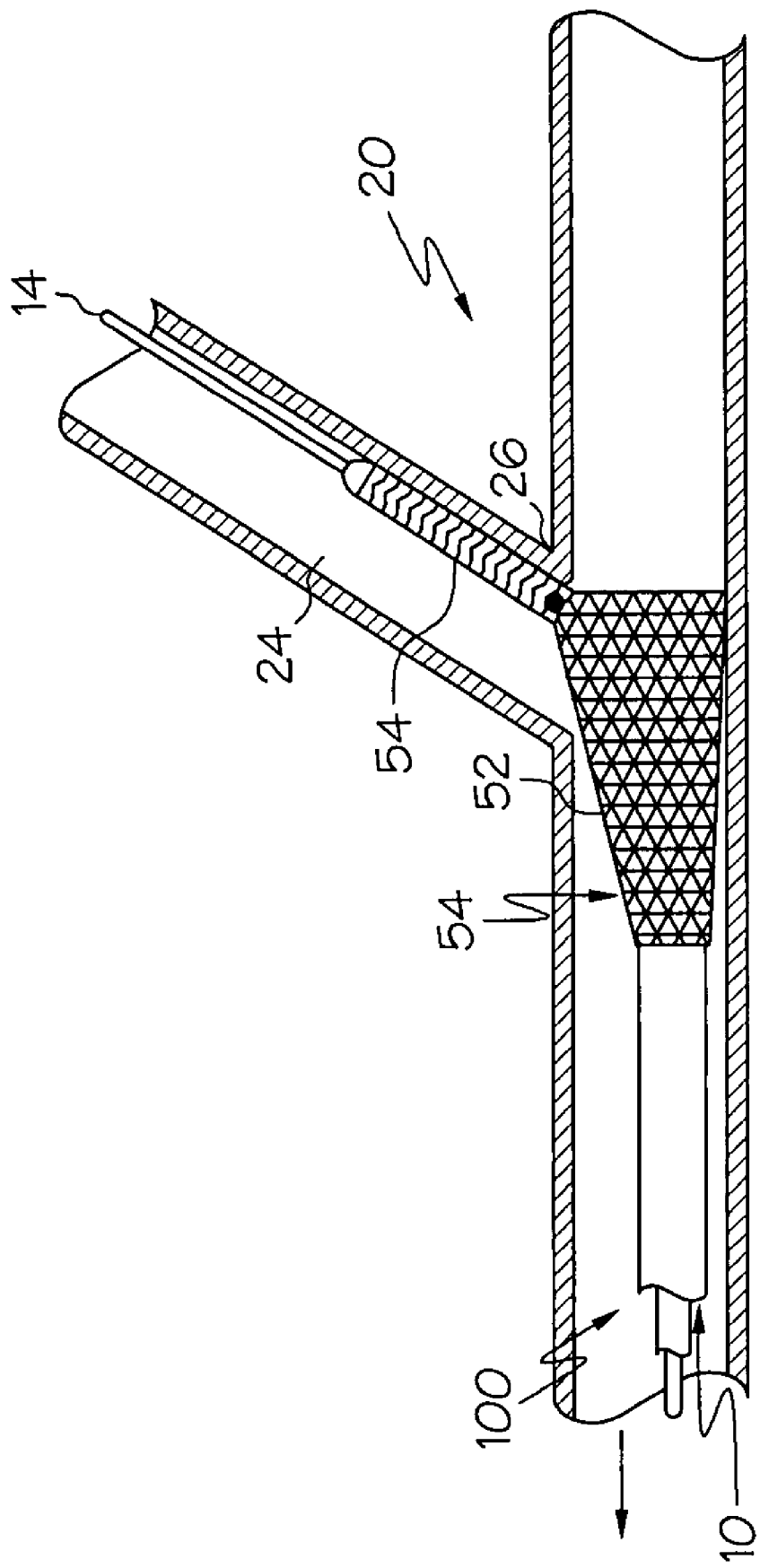
FIG. 17 is a side view of a bifurcated stent wherein the primary stent section does not extend substantially beyond the carina when deployed.

In at least one embodiment of the invention shown in FIG. 17, stent 50 includes a primary stent section 52 which does not extend distally beyond the carina 26. As a result the stent 50 may be advanced and positioned at the bifurcation site 20 by a singe guide wire 14 which extends into the secondary branch 24. Use of a marker 90 allows a practitioner to position the stent 50 by abutting the marker adjacent to the carina 26 and deploying the stent as shown. The stent 50 may include sections that are either balloon expandable, self-expandable, or hybrid expandable as desired. In the embodiment shown, primary stent section 52 is balloon expandable, and secondary stent section 54 is self-expandable.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A bifurcated stent, the bifurcated stent comprising:
a primary stent section, the primary stent section being balloon expandable, the primary stent section having a tubular wall, a first end, and a second end, the first end defining a proximal opening, the second end defining a distal opening, the primary stent section being expanded from an unexpanded configuration to an expanded configuration, in the expanded configuration the primary stent section defining a primary flow path between the proximal opening and the distal opening, the tubular wall of the primary stent section defining a side branch opening; and
a secondary stent section, the secondary stent section being self-expanding, an end of the secondary stent section being engaged to a portion of the tubular wall of the primary stent section defining the side branch opening, the secondary stent section having an unexpanded configuration and an expanded configuration, the secondary stent section having a first length in the unexpanded configuration, the secondary stent section having a second length in the expanded configuration, the first length less than the second length, the secondary stent section being expanded to the expanded configuration after the primary stent section is expanded to the expanded configuration, in the unexpanded configuration at least a portion of the secondary stent section forming a portion of the tubular wall of the primary stent section, in the expanded configuration the secondary stent section being positioned within a secondary vessel of the bifurcation site and defining a secondary flow path, the secondary flow path being in fluid communication with the primary flow path through the side branch opening.

2. The bifurcated stent of claim 1, the end of the secondary stent section being removeably engaged to the portion of the tubular wall of the primary stent section defining the side branch opening.

3. The bifurcated stent of claim 1, the secondary stent section and the primary stent section being integrally formed.

4. The bifurcated stent of claim 1, the primary stent section having a first geometry, the secondary stent section having a second geometry, the first geometry different than the second geometry.

5. The bifurcated stent of claim 1, further comprising a delivery system, the delivery system comprising a catheter, the catheter comprising:
an expandable balloon, the bifurcated stent being disposed about the expandable balloon;
a proximal housing and a distal housing, the proximal housing and the distal housing each having a closed configuration and open configuration, the proximal housing and the distal housing being immediately adjacent to one another to define a split region in the closed configuration, a portion of the proximal housing being disposed about a portion of the bifurcated stent in the closed configuration, a portion of the distal housing being disposed about a portion of the bifurcated stent in the closed configuration, the proximal housing and the distal housing in the open configuration being separated to enlarge the split region and expose the bifurcated stent;
a secondary guide wire, the secondary guide wire being positioned between the bifurcated stent and the expandable balloon, the secondary guide wire extending through the split region into a secondary vessel to guide the secondary stent section into the secondary vessel; and
a pusher mechanism, the pusher mechanism being engaged to the secondary guide wire, the pusher mechanism constructed and arranged to initiate expansion of the secondary stent section from the unexpanded configuration to the expanded configuration.

6. The bifurcated stent of claim 5, the pusher mechanism providing at least one stimulus to the secondary stent section in the unexpanded state to initiate expansion, the at least one stimulus selected from the group consisting of a predetermined electric stimulus, a predetermined mechanical stimulus, a predetermined chemical stimulus, a predetermined temperature stimulus, and any combination thereof.

7. The bifurcated stent of claim 5, wherein at least one of the proximal housing and the distal housing is selected from the group consisting of a retractable sleeve, retractable sheath, retractable sock, and any combination thereof.

8. The bifurcated stent of claim 1, further comprising at least one radiopaque marker.

* * * * *